(12) United States Patent
Dadsetan et al.

(10) Patent No.: US 12,163,020 B2
(45) Date of Patent: Dec. 10, 2024

(54) BIODEGRADABLE POLYMER BLENDS FOR MANUFACTURING MEDICAL DEVICES

(71) Applicant: Evonik Operations GmbH, Essen (DE)

(72) Inventors: Mahrokh Dadsetan, Birmingham, AL (US); Jose Santiago-Anadon, Homewood, AL (US); Balaji Prabhu, Hoover, AL (US); Andreas Karau, Gelnhausen (DE)

(73) Assignee: Evonik Operations GmbH, Essen (DE)

( * ) Notice: Subject to any disclaimer, the term of this patent is extended or adjusted under 35 U.S.C. 154(b) by 901 days.

(21) Appl. No.: 17/256,957

(22) PCT Filed: Jun. 28, 2019

(86) PCT No.: PCT/EP2019/067325
§ 371 (c)(1),
(2) Date: Dec. 29, 2020

(87) PCT Pub. No.: WO2020/002600
PCT Pub. Date: Jan. 2, 2020

(65) Prior Publication Data
US 2021/0122916 A1    Apr. 29, 2021

Related U.S. Application Data

(60) Provisional application No. 62/692,188, filed on Jun. 29, 2018.

(51) Int. Cl.
| | |
|---|---|
| *C08L 67/04* | (2006.01) |
| *A61L 27/26* | (2006.01) |
| *A61L 27/48* | (2006.01) |
| *B33Y 70/00* | (2020.01) |
| *B33Y 80/00* | (2015.01) |
| *C08K 3/32* | (2006.01) |

(52) U.S. Cl.
CPC ............ *C08L 67/04* (2013.01); *A61L 27/26* (2013.01); *A61L 27/48* (2013.01); *B33Y 70/00* (2014.12); *B33Y 80/00* (2014.12); *C08K 3/32* (2013.01); *C08K 2003/325* (2013.01); *C08K 2201/018* (2013.01); *C08L 2201/06* (2013.01)

(58) Field of Classification Search
CPC .......... C08L 67/04; C08K 3/32; B33Y 70/00; B33Y 80/00
USPC ........................................................ 523/124
See application file for complete search history.

(56) References Cited

U.S. PATENT DOCUMENTS

| | | |
|---|---|---|
| 4,844,854 A | 7/1989 | Kaplan et al. |
| 5,475,063 A | 12/1995 | Kaplan et al. |
| 6,583,232 B1 | 6/2003 | Brown |
| 6,607,548 B2 | 8/2003 | Pohjonen et al. |
| 8,486,135 B2 | 7/2013 | Wang et al. |
| 2008/0081063 A1 | 4/2008 | Wang et al. |
| 2010/0093946 A1 | 4/2010 | Thatcher et al. |
| 2013/0274422 A1 | 10/2013 | Carpentier et al. |
| 2015/0165096 A1 | 6/2015 | Andjelic et al. |

FOREIGN PATENT DOCUMENTS

| | | | |
|---|---|---|---|
| EP | 1462124 A1 | 9/2004 | |
| WO | WO-2015095266 A1 * | 6/2015 | ........... A61B 17/064 |

OTHER PUBLICATIONS

PCT International Search Report and The Written Opinion of the International Searching Authority mailed Sep. 16, 2019 corresponding to PCT Application No. PCT/EP2019/067325 filed Jun. 28, 2019 (11 pages).

* cited by examiner

*Primary Examiner* — Deve V Hall
(74) *Attorney, Agent, or Firm* — Linda S. Li; Jason S. Ngui; Andrew H. Chung

(57) ABSTRACT

The present invention is directed to bioresorbable polymer blend compositions with tunable mechanical properties for manufacturing medical devices. These blends are multicomponent blends, comprise multiple polymer components and may or may not require additives in the form of fibers or particles for the potential enhancement of mechanical and/or biological properties.

18 Claims, 32 Drawing Sheets

US 12,163,020 B2

BIODEGRADABLE POLYMER BLENDS FOR MANUFACTURING MEDICAL DEVICES

This Application is a 35 U.S.C. § 371 U.S. national stage of PCT International Application No. PCT/EP2019/067325, filed Jun. 28, 2019, which claims the benefit of U.S. Provisional Patent Application No. 62/692,188, filed Jun. 29, 2018, the contents of each of which are hereby incorporated by reference in their entirety into this application.

FIELD OF THE INVENTION

The presently disclosed invention relates to novel polymer composition containing multicomponent polymer blends and their composites with inorganic additives. Reinforcement of said polymer blends with fibers is also disclosed. These polymer blends provide tailored mechanical properties suitable for use in medical devices.

DESCRIPTION OF RELATED ART

Biodegradable polymer blends and their use in medical device manufacturing are known. Below you see some examples: U.S. Pat. Nos. 4,844,854; 5,475,063; 6,583,232; 6,607,548; 8,486,135

Polymer blends in this invention relate to novel multicomponent polymer blends with improved ductility, toughness and impact resistance. The polymer matrix can be chosen from both amorphous and semi-crystalline materials. When the matrix is chosen from semi-crystalline materials, higher crystallinity and increased modulus can be achieved. In addition, semi-crystalline matrix used in multicomponent blends enables annealing of polymer blend to enhance impact strength of polymer blends. In this invention, the effect of aging is minimized with incorporation of second polymer additive that improves phase miscibility. In two component blends, elongation at break decreases with aging due to chain reorganization. This is in contrast to previously disclosed inventions such as U.S. Pat. No. 6,607,548. The polymer blends in presently disclosed invention can be extruded and drawn into-mono- or multifilament fibers with improved mechanical properties or processed into filaments for 3D printing. The polymer blends may incorporate inorganic additives and/or fibers as reinforcement agents for particular applications in orthopedics. We also describe addition of coloring agents such as D&C Violet NO. 2, D&C Green NO. 6, and D&C Blue NO. 6 for application in soft tissue repair.

SUMMARY OF THE INVENTION

The polymer blend composition is a multicomponent polymer blend comprising a base polymer derived from lactide or glycolide based polymers or copolymers (50-95% w/w) and one or more secondary polymers comprising polycaprolactone and polyethylene carbonate copolymers (5-50% w/w). Said polymer blends are compounded into granules and may be injection molded into flexural and tensile bars for mechanical testing or into other articles for medical device manufacture. Ductility of these polymer blends can be tuned with change in blend composition. With change in blend formulation, an elongation at break ranging from about 10% to about 200% can be attained. Moreover, a post-processing annealing treatment of the tensile and flexural bars was shown to be capable of achieving even higher values for the strength and modulus of the blends which is possibly due to the increase in crystallinity observed after the annealing process. Further, the polymer blends showed improved impact resistance and toughness. Compounding of polymer blends with inorganic additive particles is also described as a means by which even higher mechanical properties, such as modulus, can be achieved. These polymer blends containing inorganic additives, known hereafter as polymer blend composites, can be used in manufacturing of orthopedic medical devices.

Fiber reinforcement has been applied to improve mechanical properties of polymer blends for load bearing applications. Fibers can be added to the matrix at the concentration of (1-50% w/w) as continuous or chopped fibers via a melt processing approach. Fibers are selected from biodegradable and/or non-degradable fibers. Degradable fibers may include but not limited to polylactide, (PLA), Polyglycolide (PGA), poly(lactic-co-glycolic acid) (PLGA), polycaprolactone (PCL), polydioxanone (PDO), and their copolymers and non-degradable fibers may include but not limited to poly(vinyl alcohol) (PVA), polyetheretherketone (PEEK), polybutylene terephthalate (PBT), and polyethylene terephtalate (PET). Hereafter, these fiber containing polymer blends are defined as fiber reinforced polymer blend composites. Process of multicomponent blend composition disclosed herein into reinforced composites and into extruded filaments and drawn fibers is described.

BACKGROUND OF THE INVENTION

There is a growing interest for use of bioresorbable biomaterials in implantable medical devices. Polylactic acid (PLA) homo-polymers such as PLLA and its copolymers are favorable for use in implantable medical devices due to their excellent biocompatibility and handling properties. Further, these polymers degrade in the body and their degradation products are metabolized via Krebs cycle. PLA-based polymers also have a tensile strength and modulus that is appropriate for a number of applications in medical devices. However, their application is limited due to their brittleness. This brittleness is evident in PLA-based polymers lack of fracture toughness and elongation at fracture, which inhibits their use in particular applications such as orthopedic devices and ligating clips. In order to make PLA-based polymer materials a more desirable choice in the area of orthopaedic devices and ductile medical articles (e.g., ligating clips), the invention presented herein discloses novel compositions shown to exhibit the proper mechanical properties for manufacturing such medical devices.

DETAILED DESCRIPTION OF THE INVENTION

Figure 1A:
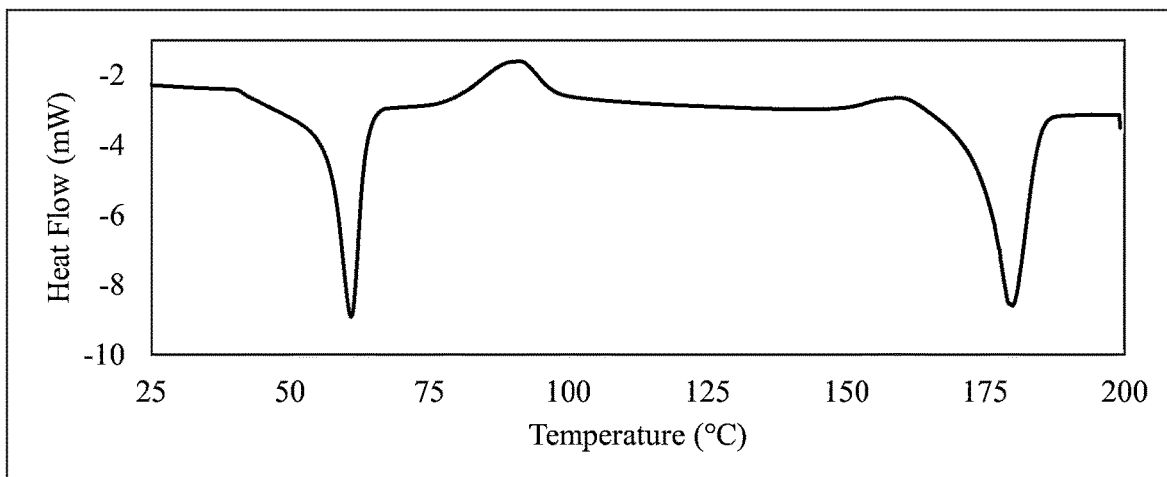
FIG. 1A depicts a thermogram of a differential scanning calorimetry analysis showing two separate melting curves for each component of the immiscible polymer blend containing a weight-to-weight blend of 70% PLLA and 30% PCL.
Figure 1B:
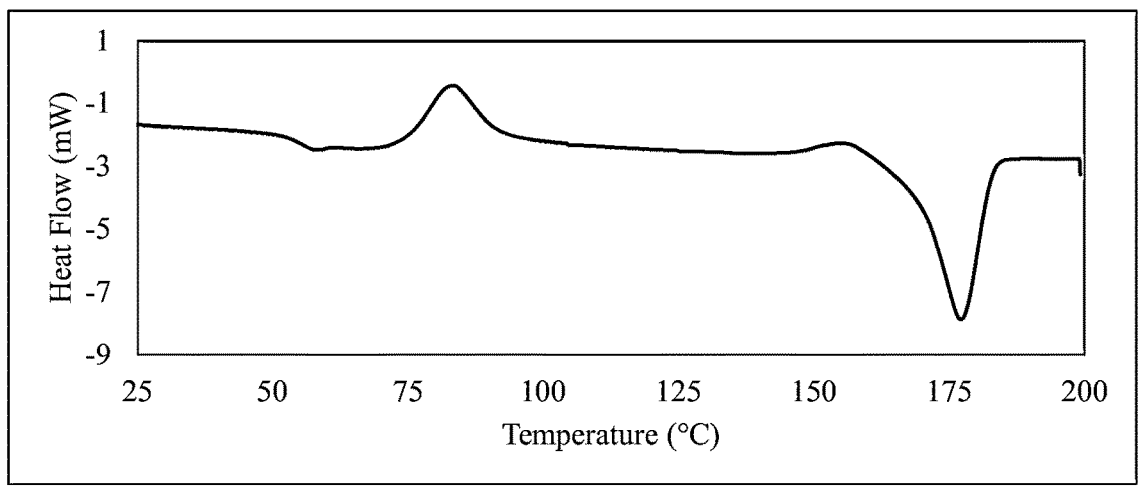
FIG. 1B depicts a thermogram of a differential scanning calorimetry analysis showing a single melting curve verifying the miscibility of the polymer blend containing a weight-to-weight blend of 70% PLLA and 30% PLLA-co-PCL 70:30.
Figure 1C:
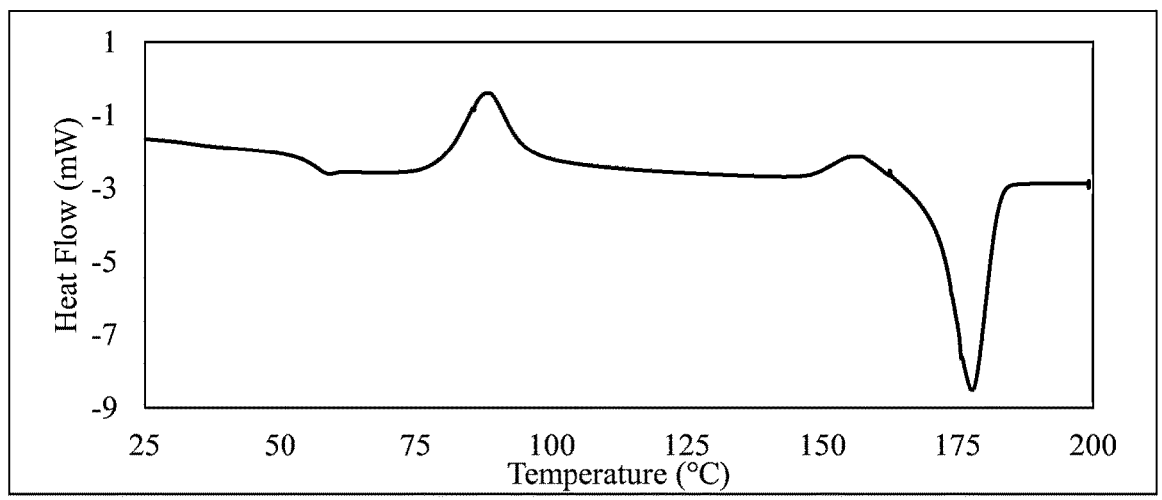
FIG. 1C depicts a thermogram of a differential scanning calorimetry analysis showing a single melting curve verifying the miscibility of the polymer blend containing a weight-to-weight blend of 70% PLLA and 30% PLLA-co-TMC 70:30.
Figure 1D:
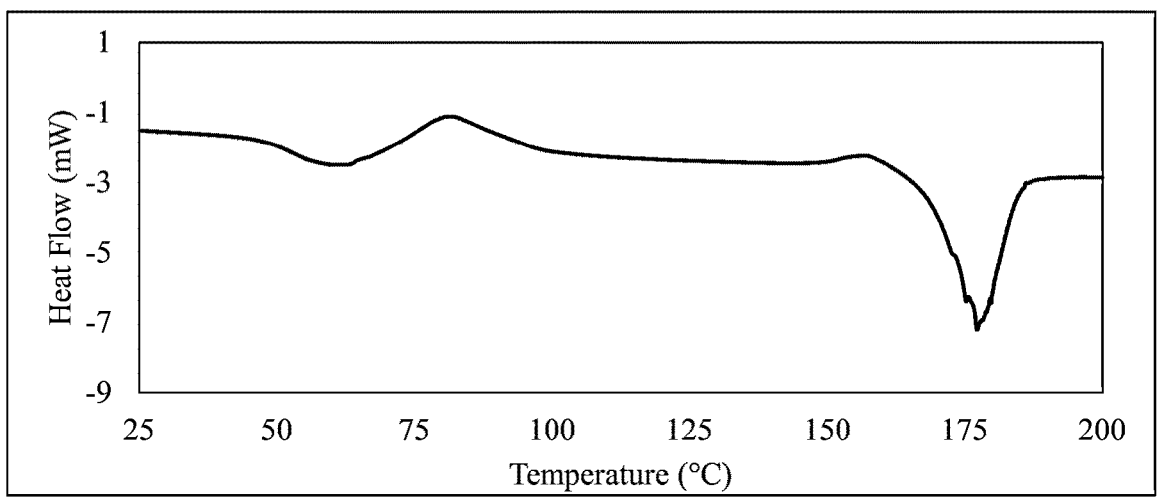
FIG. 1D depicts a thermogram of a differential scanning calorimetry analysis showing a single melting curve verifying the miscibility of the polymer blend containing a weight-to-weight blend of 75% PLLA, 15% PLLA-co-TMC 70:30 and 10% PLLA-co-PCL 70:30.

For the purpose of promoting a thorough understanding of the presently disclosed invention and not as a limitation of potential future embodiments of the herein disclosed invention, below are given examples of potential embodiments of the herein disclosed invention with reference made to specific embodiments with specific language being used to describe the same. It is therefore to be understood that no limitation of the scope of the herein disclosed invention shall be read into the preferred embodiment examples herein described or further modifications of the disclosed invention, with such further modifications and/or applications being those which would occur normally to one skilled in the art of the herein disclosed invention and related fields of study.

DEFINITION OF TERMS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The conjunctive term "or" includes any and all combinations of one or more listed elements associated by the conjunctive term. For example, the phrase "an apparatus comprising A or B" may refer to an apparatus including A where B is not present, an apparatus including B where A is not present, or an apparatus where both A and B are present. The phrases "at least one of A, B, . . . and N" or "at least one of A, B, . . . N, or combinations thereof" are defined in the broadest sense to mean one or more elements selected from the group comprising A, B, . . . and N, that is to say, any combination of one or more of the elements A, B, . . . or N including any one element alone or in combination with one or more of the other elements which may also include, in combination, additional elements not listed.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The term "wt. %" means weight percent.

The term "w/w" means weight per weight.

For the purposes of the present invention, the term "biodegradable" refers to polymers that dissolve or degrade in vivo within a period of time that is acceptable in a particular therapeutic situation. Such dissolved or degraded product may include a smaller chemical species. Degradation can result, for example, by enzymatic, chemical and/or physical processes. Biodegradation takes typically less than five years and usually less than one year after exposure to a physiological pH and temperature, such as a pH ranging from 6 to 9 and a temperature ranging from 22° C. to 40° C.

For the purposes of the present invention, the term "additive manufacturing" includes, but are not limited to, bioplotter, fused filament fabrication (FFF), selective laser sintering (SLS), and stereolithography (SLA). A 3D printed part can also be a bioprinted part.

For the purposes of the present invention, the term "miscible" means forming a continuous homogenous phase.

For the purposes of the present invention, the term "radiopacity" means being visualized by x-ray.

The present invention relates to the production of blended polymer compositions and polymer composites with increased desired mechanical properties without changing the biological properties adversely wherein said polymer composites may contain fibers and/or particles. In certain embodiments of the invention, the compositions include a blend of virgin polymeric constituents whereas other preferred embodiments of the disclosed invention include fibrous material along with the polymeric blend which are able to further increase the desired mechanical properties. Further, embodiments of the presently disclosed invention may contain inorganic additive particles within the polymer blend for the enhancement of both mechanical and biological properties of the polymer blend composite.

Figure 2:
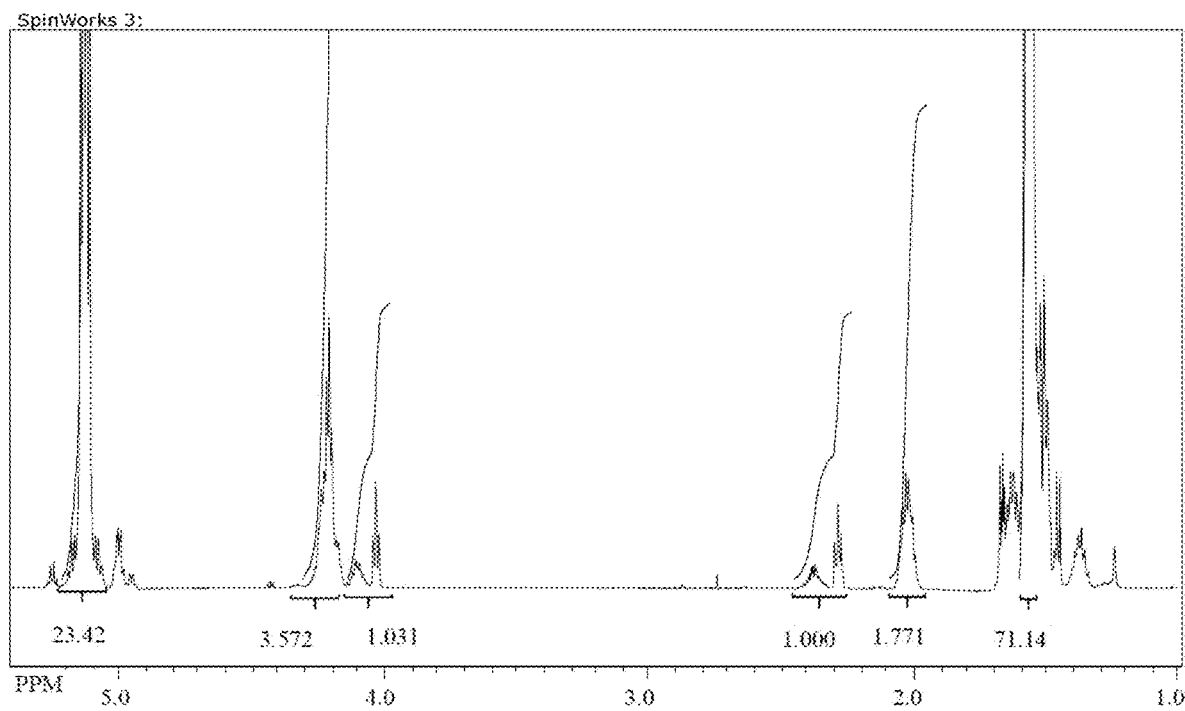
FIG. 2 depicts NMR spectra of the copolymer ratios in the multiphase polymer blend comprising a weight-to-weight blend of 75% PLLA, 15% PLLA-co-TMC, and 10% 70:30 PLLA-co-PCL.
Figure 3A:
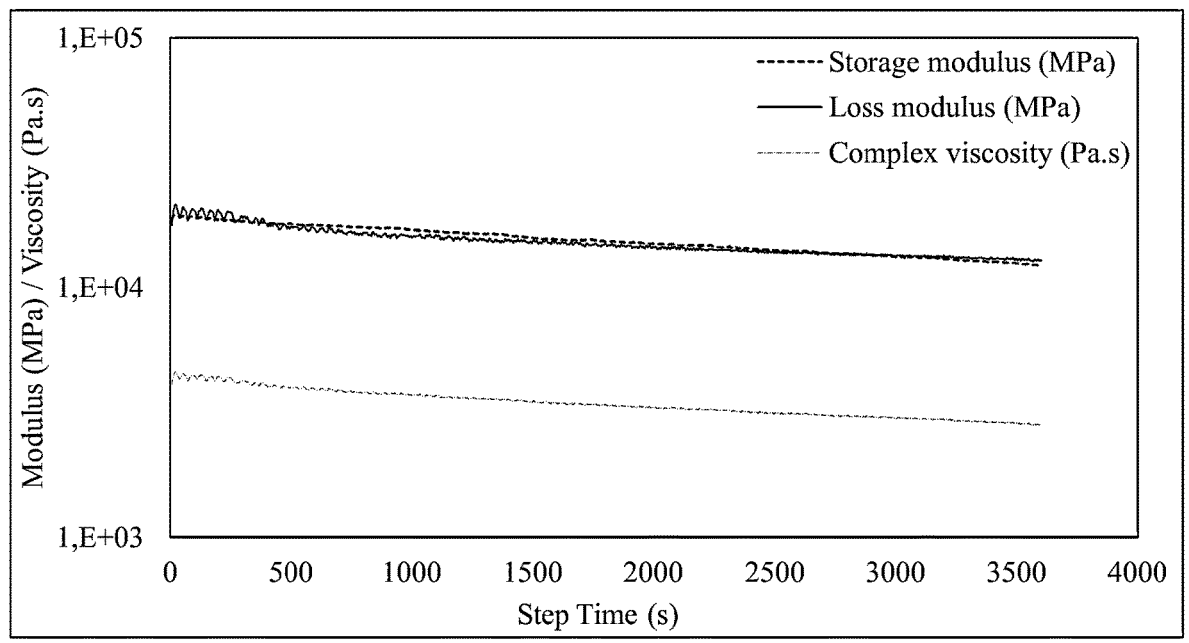
FIG. 3A depicts rheological results of the polymeric blends containing PLLA+15% PLLA-co-TMC+10% PLLA-co-PCL with the change in complex viscosity, storage modulus, and loss modulus as a function of time.
Figure 3B:
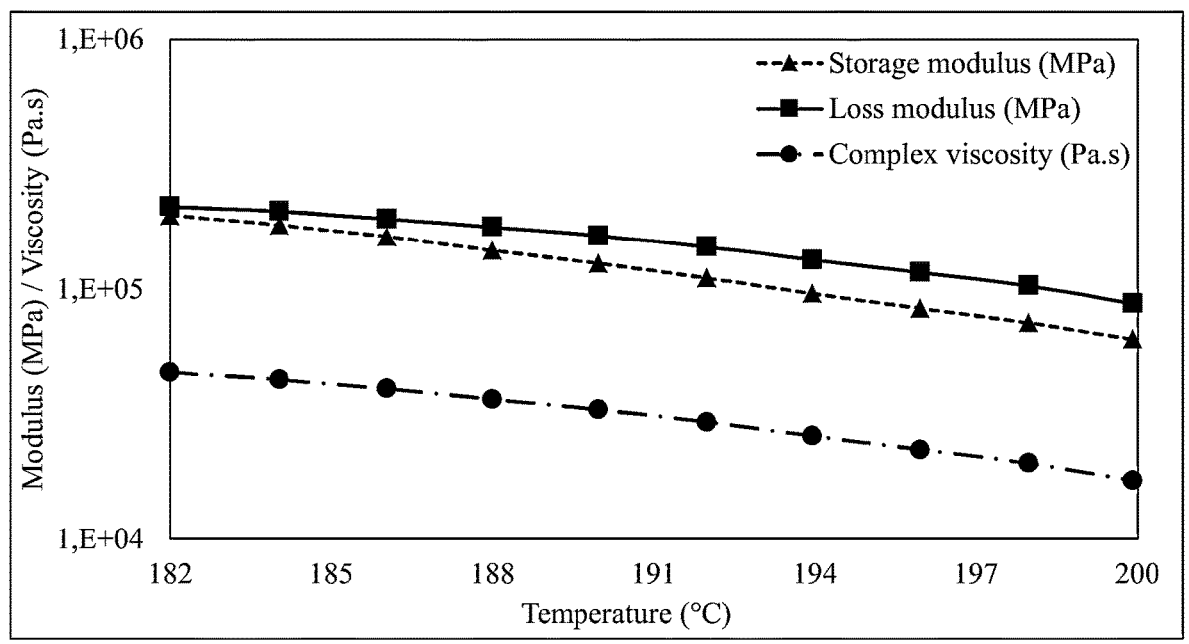
FIG. 3B depicts rheological results of the polymeric blends containing PLLA+15% PLLA-co-TMC+10% PLLA-co-PCL as a function of temperature.

The herein disclosed invention aims to address of the brittleness of medical device articles comprising polylactide homopolymers (e.g., PLLA) and polylactide copolymers (e.g., PLGA, poly-L-lactide-co-DL-lactide, PLDLLA) that has been a limitation to the use of such materials for a number of applications including load-bearing applications. As stated, the brittleness of polylactide homopolymers (e.g. PLLA) and copolymers (e.g. PLGA or PLDLLA) can be reduced with blending with polymers or copolymers with more ductility such as polycaprolactone (PCL) and poly (trimethylene carbonate) (PTMC). However, PCL and PTMC are immiscible with polylactide polymers and copolymers resulting in phase separation which can be seen quantitatively from multiple melting peaks in thermal methods such as differential scanning calorimetry. The present disclosure provides implantable polymer blends where a continuous phase was formed by melt blending of the polymer matrix and polymer additives such as poly(L-lactide-co-caprolactone)70:30 (PLLA-co-PCL) and poly(L-lactide-co-trimethylene carbonate)70:30 (PLLA-co-TMC) where the miscibility of these blends can be seen quantitatively as the presence of a single melting curve in differential scanning calorimetry (FIG. 1). A wide variety of methods are available for polymer blending including, melt blending, solvent blending, dry powder mixing, solid state pulverizing and supercritical carbon dioxide blending. In one aspect of this disclosure, a method is provided wherein a twin-screw extruder is used to blend the base polymer matrix and additive polymers at a temperature above the melting temperature of all ingredients (180° C.-220° C.). Further, the polymers were pre-mixed at the desired ratios using a tumbler blender for approximately 30 min and subsequently fed into the extruder using a gravimetric feeder. The resulting blends were collected and the molar ratio of polymers in the blends was determined using $H_1NMR$ (FIG. 2). The polymer blends in the present application consist of a polymer matrix based on PLA homopolymer or copolymers with glycolic acid or DL-Lactide (50-95%) and at least one secondary polymer species (5-50%) that is/are selected from poly lactide copolymers, e.g., PLLA-co-TMC or PLLA-co-PCL. The polymer matrix may be semi-crystalline or amorphous. Said secondary polymer species are miscible with polymer matrix forming a continuous phase without phase separation after blending and processing. Mechanical properties of polymer blends varies with change in the blended ratio of the base polylactide-based polymer and the secondary polymer species. Similarly, the amount of the base polymer in relation to the secondary additive polymer species along with the type of secondary polymer species controls the degradation properties of the resultant polymer blends. For instance, a faster degradation is expected if PLGA is chosen as the base polymer species compared to a polymeric blend composition wherein the PLA homopolymer is selected as polymer matrix. Degradation rate of polymer blends varies with change in PLLA-co-TMC and PLA-co-PCL content. Above mentioned polymer compositions can be compounded at a lower temperature than base polymers conventional processing. Rheological behavior of ternary blend based on PLLA with 15 wt % PLLA-co-TMC and 10% PLA-co-PCL additive polymers is shown in FIG. 3.

Figure 4A:
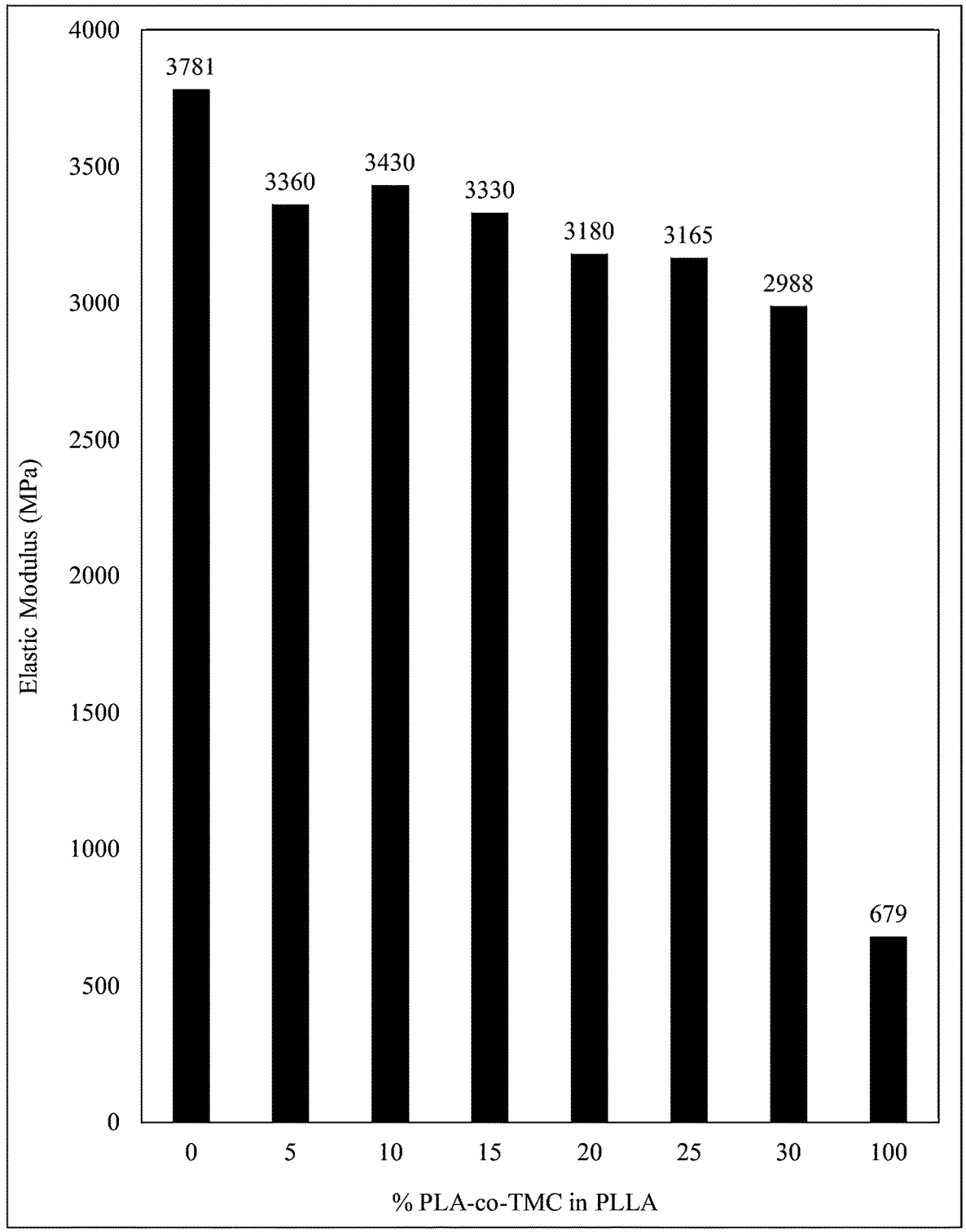
FIG. 4A depicts the effect of polymer ratio in the weight-to-weight blends containing PLLA and PLLA-co-TMC on the elastic modulus of polymer blends.
Figure 4B:
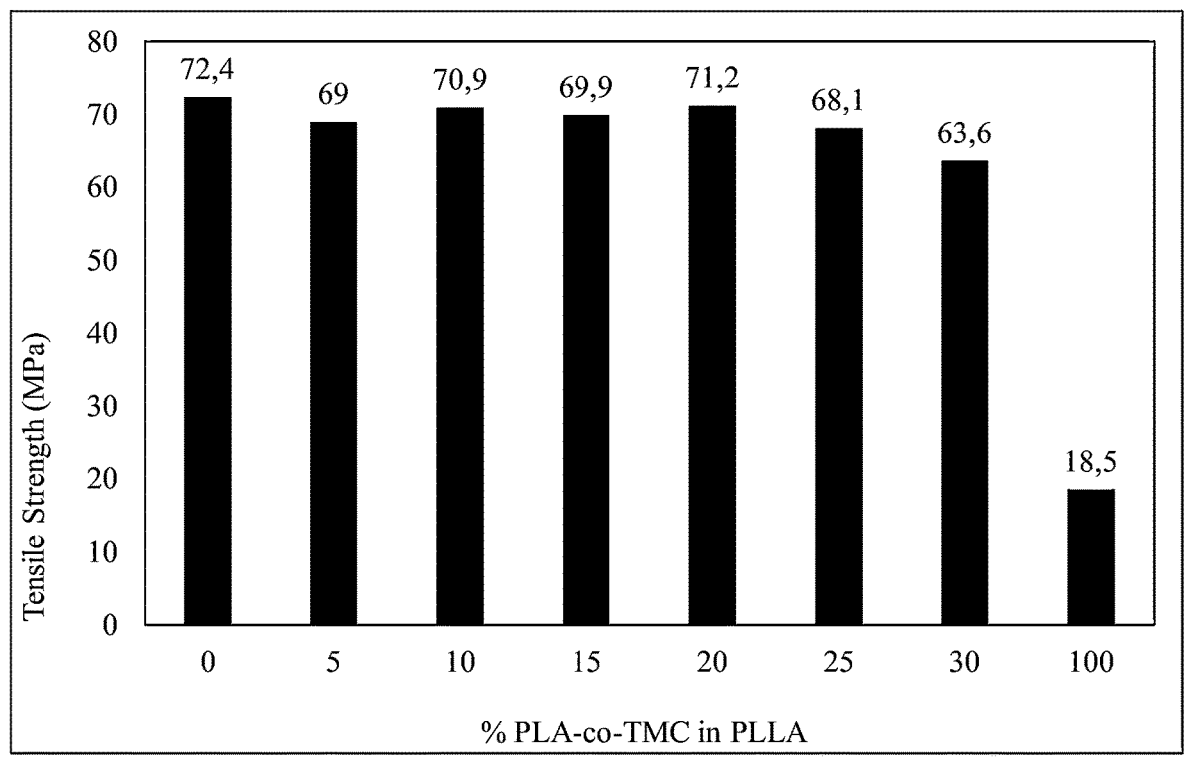
FIG. 4B depicts the effect of polymer ratio in the weight-to-weight blends containing PLLA and PLLA-co-TMC on the tensile strength of the polymer blends.
Figure 4C:
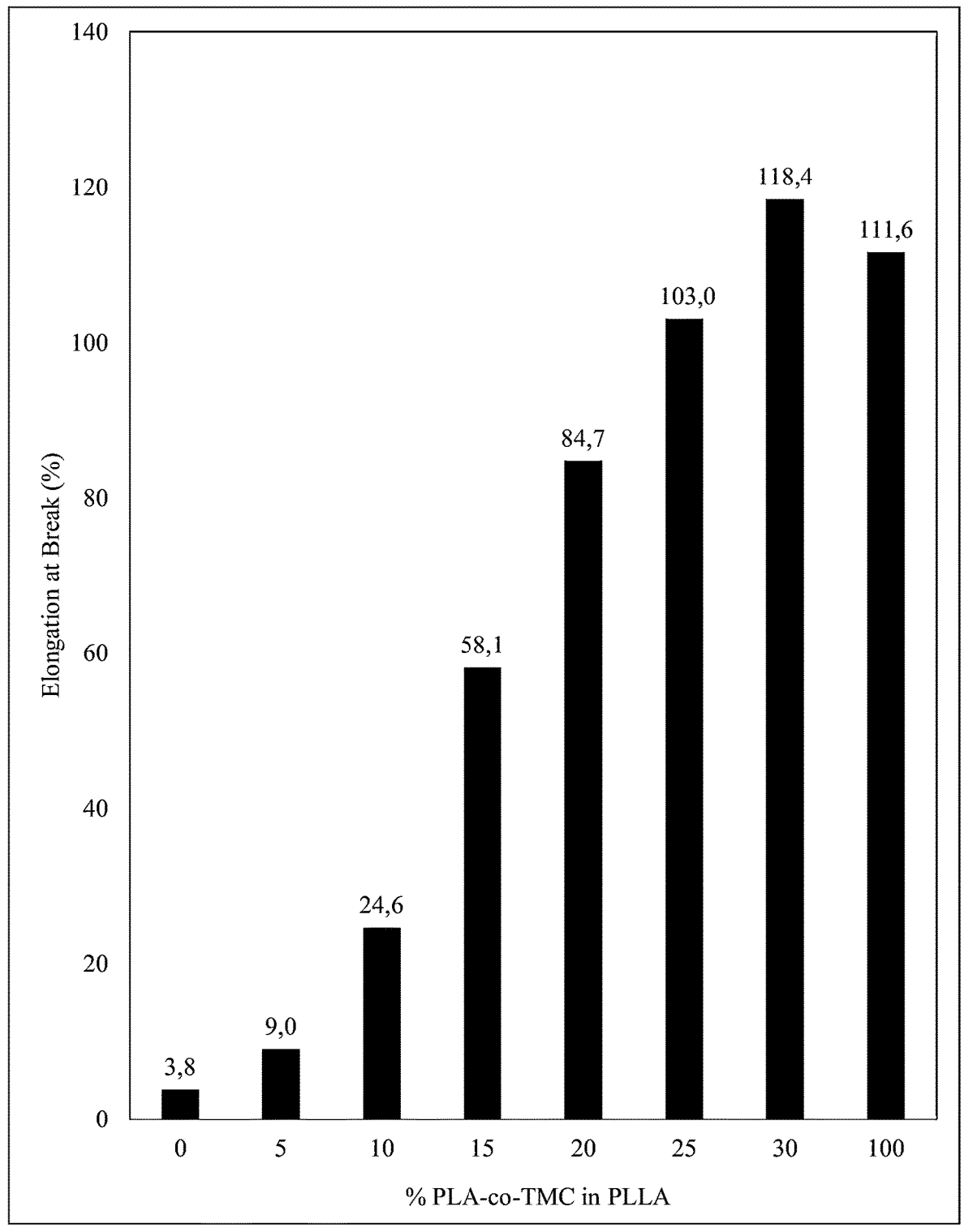
FIG. 4C depicts the effect of polymer ratio in the weight-to-weight blends containing PLLA and PLLA-co-TMC on the elongation at break of the polymer blends.

Typically, the tensile strength of the polymer matrix is reduced when blended with a soft polymer such as PCL and/or PTMC. In the present disclosure, while a slight initial change in tensile strength of the polymer blend was found when the secondary polymer species of PLLA-co-TMC was added to the PLLA base polymer, the tensile strength remained comparable for all ratios of the polymer blend until the secondary polymer species reached 30% (w/w) of the polymer blend (FIG. 4A). Further, although the modulus of the polymer blend composition comprising a PLA-based base polymer and PLLA-co-TMC as the secondary polymer species decreases with increasing secondary polymer species concentration, the elongation at break increases continuously up to 120% with addition of 30% PLLA-co-TMC (FIG. 4C).

Figure 5A:
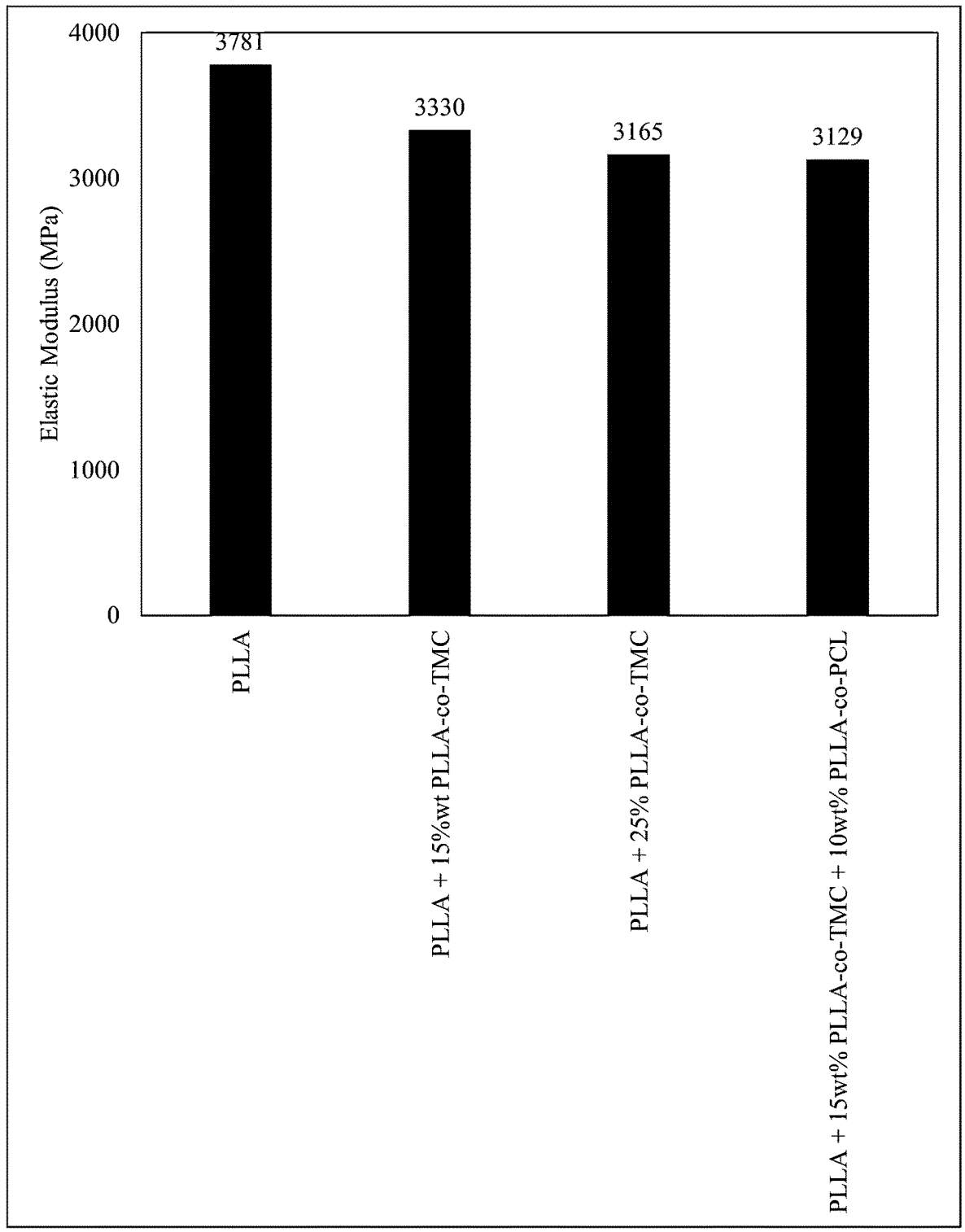
FIG. 5A depicts the effect of polymer ratio in the weight-to-weight blends containing PLLA, PLLA-co-TMC, PLLA-co-PCL and on the elastic modulus of the polymer blends.
Figure 5B:
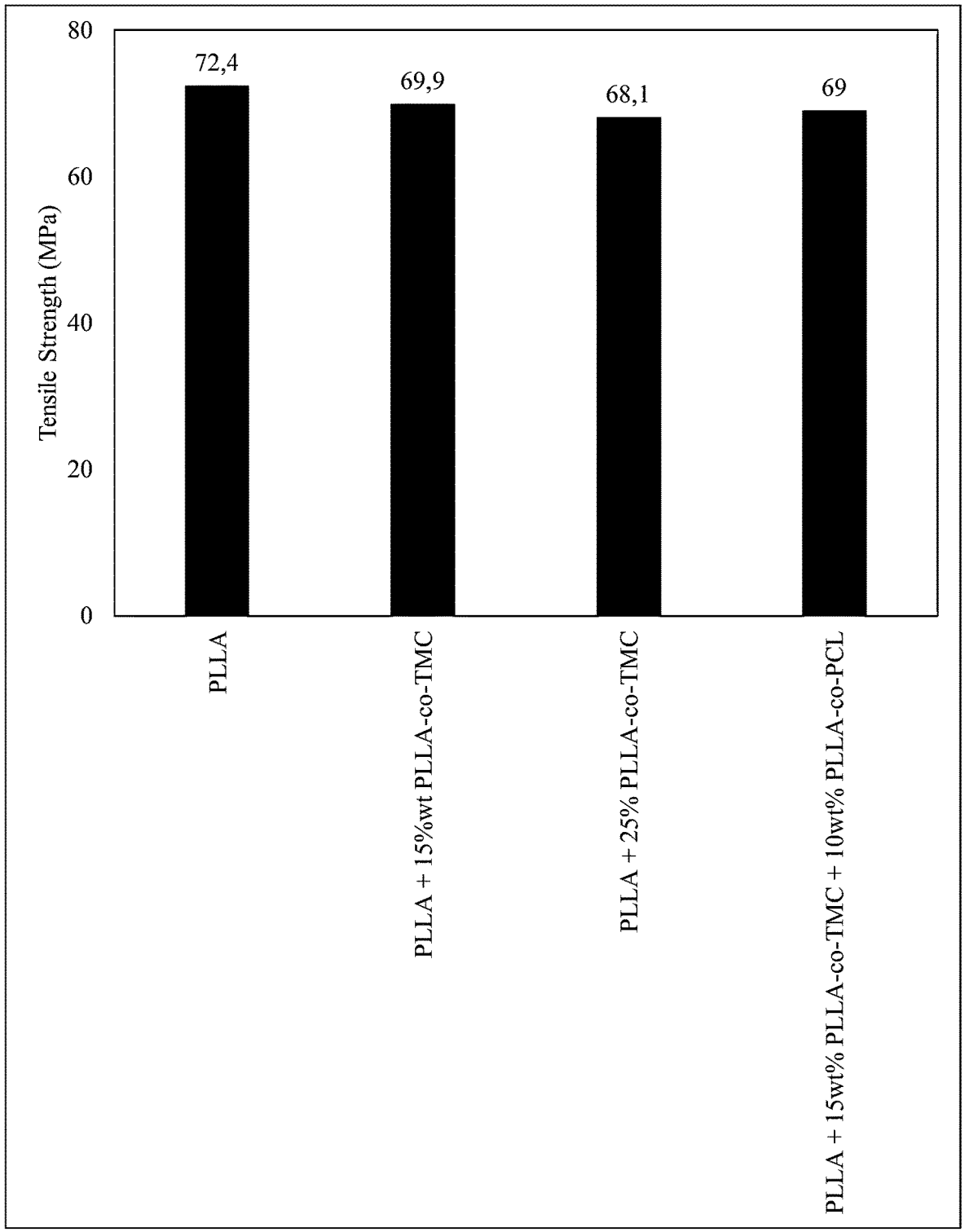
FIG. 5B depicts the effect of polymer ratio in the weight-to-weight blends containing PLLA, PLLA-co-TMC, and PLLA-co-PCL on the tensile strength of the polymer blends.
Figure 5C:
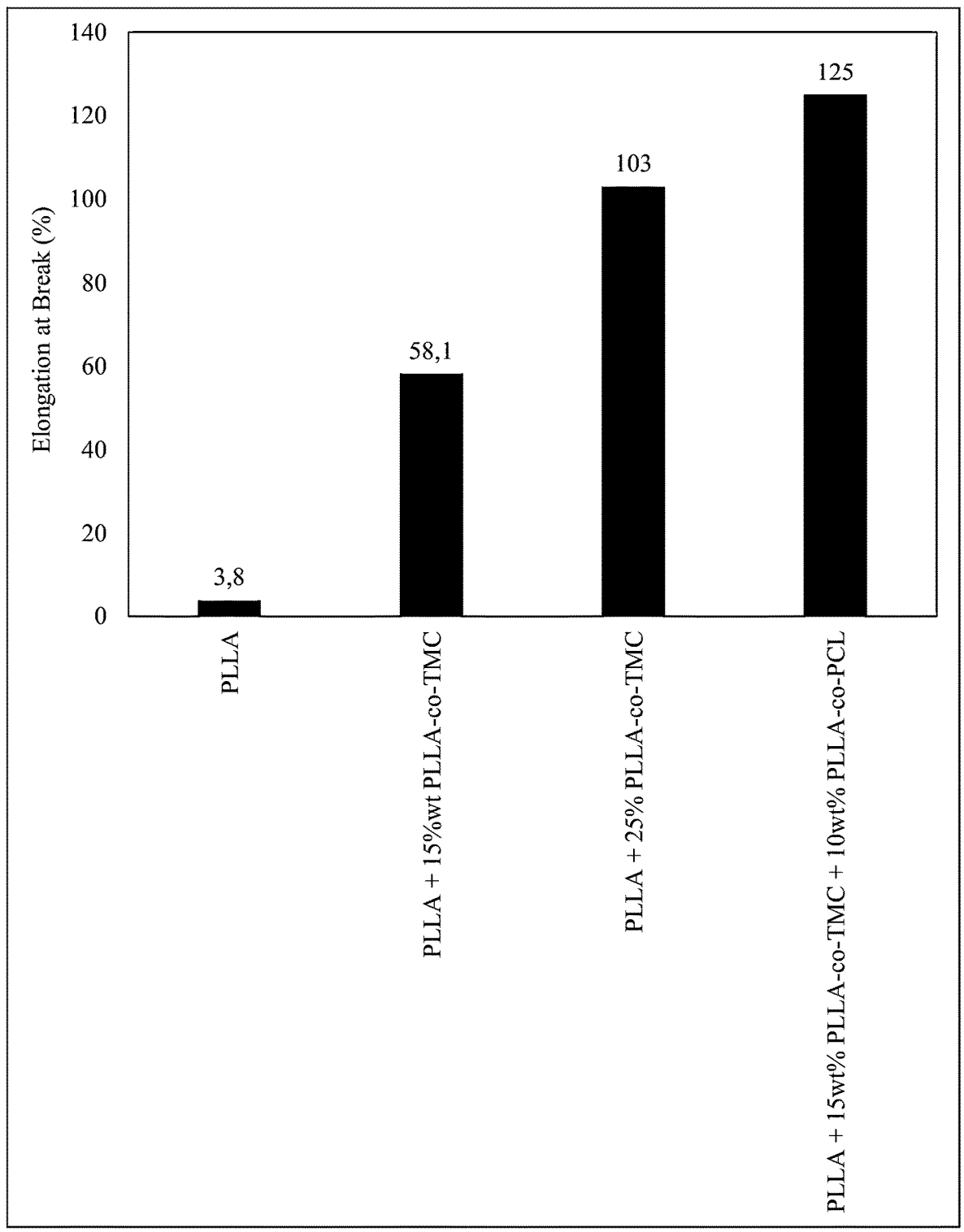
FIG. 5C depicts the effect of polymer ratio in the weight-to-weight blends containing PLLA, PLLA-co-TMC, and PLLA-co-PCL on the elongation at break of the polymer blends.

Further, the polymer blends may comprise multiple polymeric species in order to achieve greater mechanical, biological, and/or degradation properties. For instance, the addition of PLLA-co-TMC and PLLA-co-PCL to the base polymer matrix of PLA show an even greater increase in the elongation at break (i.e., ductility) of the polymer blend which may be attributed to an improvement in phase continuity upon addition of the PLLA-co-PCL (FIG. 5).

Figure 6A:
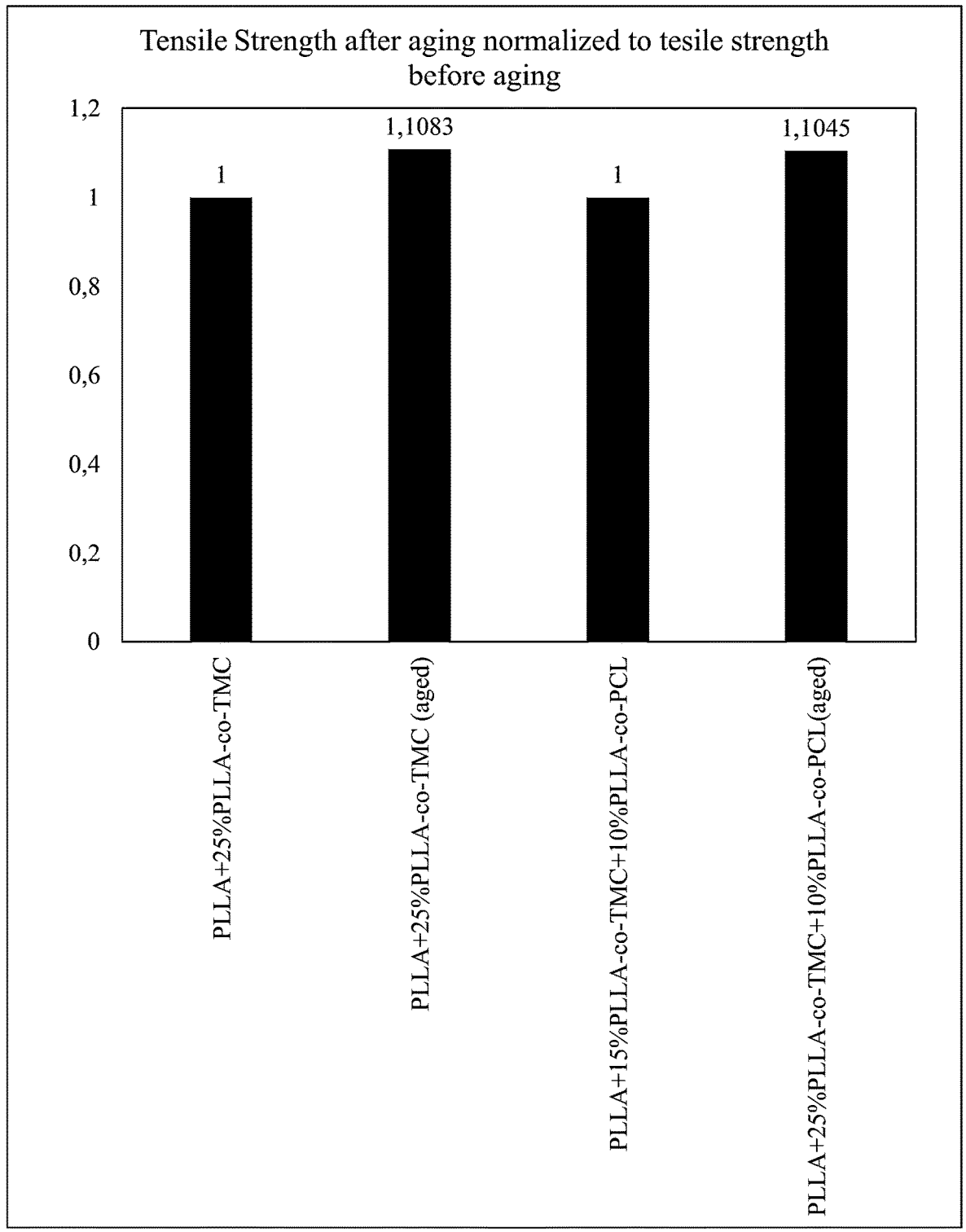
FIG. 6A depicts tensile strength of PLLA binary blends with 25 wt % PLLA-co-TMC and PLLA ternary blend with 15 wt % PLLA-co-TMC and 10 wt % PLLA-co-PCL after aging for 12 weeks
Figure 6B:
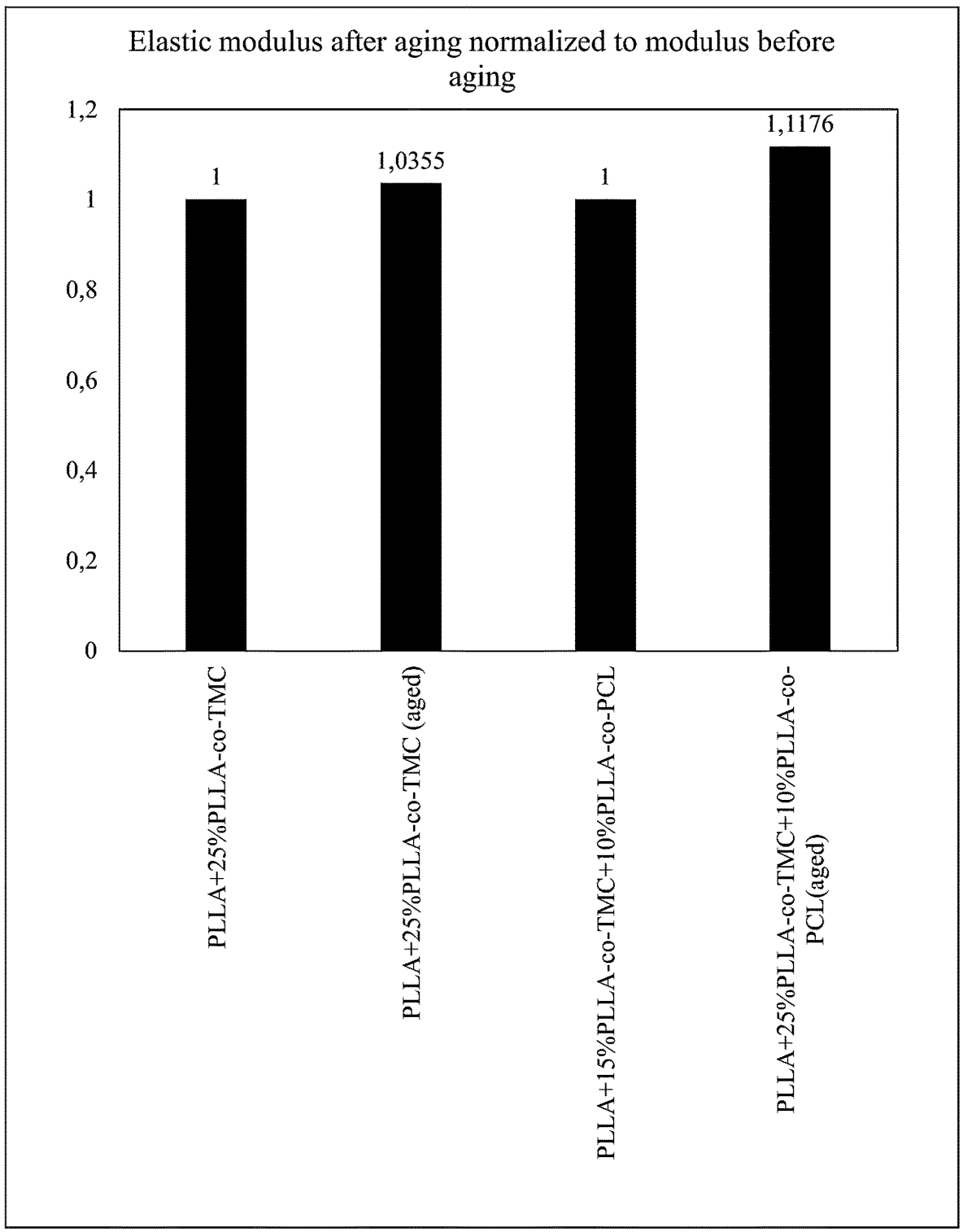
FIG. 6B depicts elastic modulus of PLLA binary blends with 25 wt % PLLA-co-TMC and PLLA ternary blend with 15 wt % PLLA-co-TMC and 10 wt % PLLA-co-PCL after aging for 12 weeks
Figure 6C:
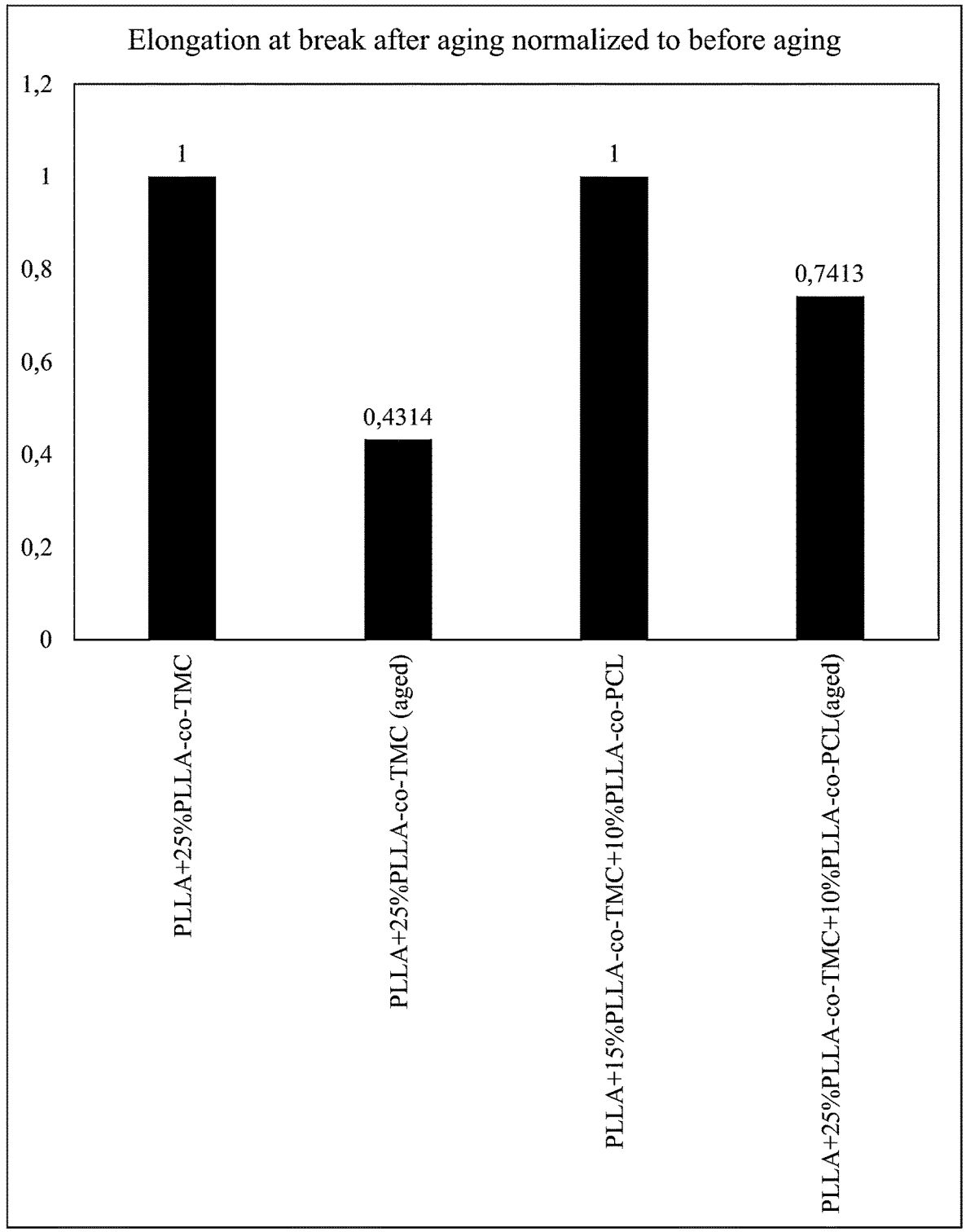
FIG. 6C depicts elongation at break of PLLA binary blends with 25 wt % PLLA-co-TMC and PLLA ternary blend with 15 wt % PLLA-co-TMC and 10 wt % PLLA-co-PCL after aging for 12 weeks

In further embodiments of the presently disclosed invention, the crystallinity of the polymer matrix can be modified so as to enhance the resulting mechanical properties of polymer blends. For instance, it is shown that the use of PLLA as the base polymer matrix results in formation of large spherulites within the matrix, which ultimately results in increase in tensile strength and modulus but decrease in ductility of polymer blends. It is shown within the presently disclosed invention that addition of PLLA-co-PCL to the binary blend consisting PLLA-co-TMC improves phase continuity which results in reducing aging effect of binary PLLA blends with PLLA-co-TMC (FIG. 6). Both tensile strength and elastic modulus of binary and ternary PLLA blends increased with aging and as expected elongation at break decreased (FIG. 6 A-C). Results in FIG. 6C demonstrates minimized aging effect on elongation break of ternary blend in comparison to binary blend with addition of 10% PLLA-co-PCL. Elongation at break of ternary blend only reduced about 25% as compared to 57% for binary blend. This contributes to ternary blend retention of cold bendability without the need for heating to recover cold bendable property as disclosed in U.S. Pat. No. 6,607,548.

An annealing process of the herein disclosed polymer blends resulted in an increase in crystallinity from less than 20% before annealing to approximately 40% after annealing. The annealing of the specimens was conducted at 80° C. for 5 h followed by slow cooling overnight. Table 1 compares mechanical property and crystallinity of annealed specimens with unannealed ones. As seen in this table, crystallinity increased through this annealing process for both PLLA and there herein disclosed polymer blends comprising PLLA as a base polymer matrix.

Further, alternative embodiments of the presently disclosed invention can allow for the adjustment of the crystallinity of the said polymer blends. For instance, a lower crystallinity has been shown the be achieved for polymer blends comprising the PLLA base polymer matrix with the secondary polymer species being 25% (w/w) PLLA-co-TMC. Similar findings were shown when the secondary polymer species comprises 15% (w/w) PLLA-co-TMC+ 10% (w/w) PLLA-co-PCL 70:30.

Tensile, flexural and impact properties of annealed and unannealed specimens are compared in table below. As seen, Modulus, stress at break, impact strength and tensile strength increased due to annealing. Usually, elongation at break of the semi-crystalline polymers decreases due to annealing. However, elongation at break of the blends with 25% PLLA-co-PCL and blend with both 15% PLLA-co-TMC and 10% PLLA-co-PCL decreased to a lesser degree (3-4×) as compared to the blends with 25% PLLA-co-TMC (6× decrease). This could be due to miscibility of PLLA-co-PCL with PLLA and its role as a compatibilizer when blended together with PLLA-co-TMC. Similar effect is seen on aging of these polymer blends. Addition of PLLA-co-PCL to the blend of PLLA/PLLA-co-TMC resulted in reduced aging effects (FIG. 6).

TABLE 1

| PLLA | PLLA-co-TMC | PLLA-co-PCL | Annealed? | Modulus (MPa) | Tensile Strength (MPa) | Elongation at Break (%) | Stress at Break (MPa) | Notched Izod Impact (kJ/m$^2$) | % Crystallinity |
|---|---|---|---|---|---|---|---|---|---|
| 100% | 0% | 0% | No | 3862 | 76.0 | 4.7 | 59.2 | 3.77 | 20 |
| 100% | 0% | 0% | Yes | 4339 | 80.6 | 4.0 | 70.0 | 6.58 | 51 |
| 75% | 25% | 0% | No | 3165 | 68.1 | 103.0 | 39.2 | — | 7 |
| 75% | 25% | 0% | Yes | 3240 | 71.2 | 16.7 | 53.8 | — | 38 |
| 75% | 0% | 25% | No | 2757 | 55.1 | 134.9 | 37.1 | — | — |
| 75% | 0% | 25% | Yes | 3406 | 64.9 | 42.2 | 50.2 | — | — |
| 75% | 15% | 10% | No | 3128 | 69.0 | 125.1 | 40.5 | 4.04 | 16 |
| 75% | 15% | 10% | Yes | 3400 | 69.6 | 31.3 | 54.3 | 5.56 | 34 |

Figure 7A:
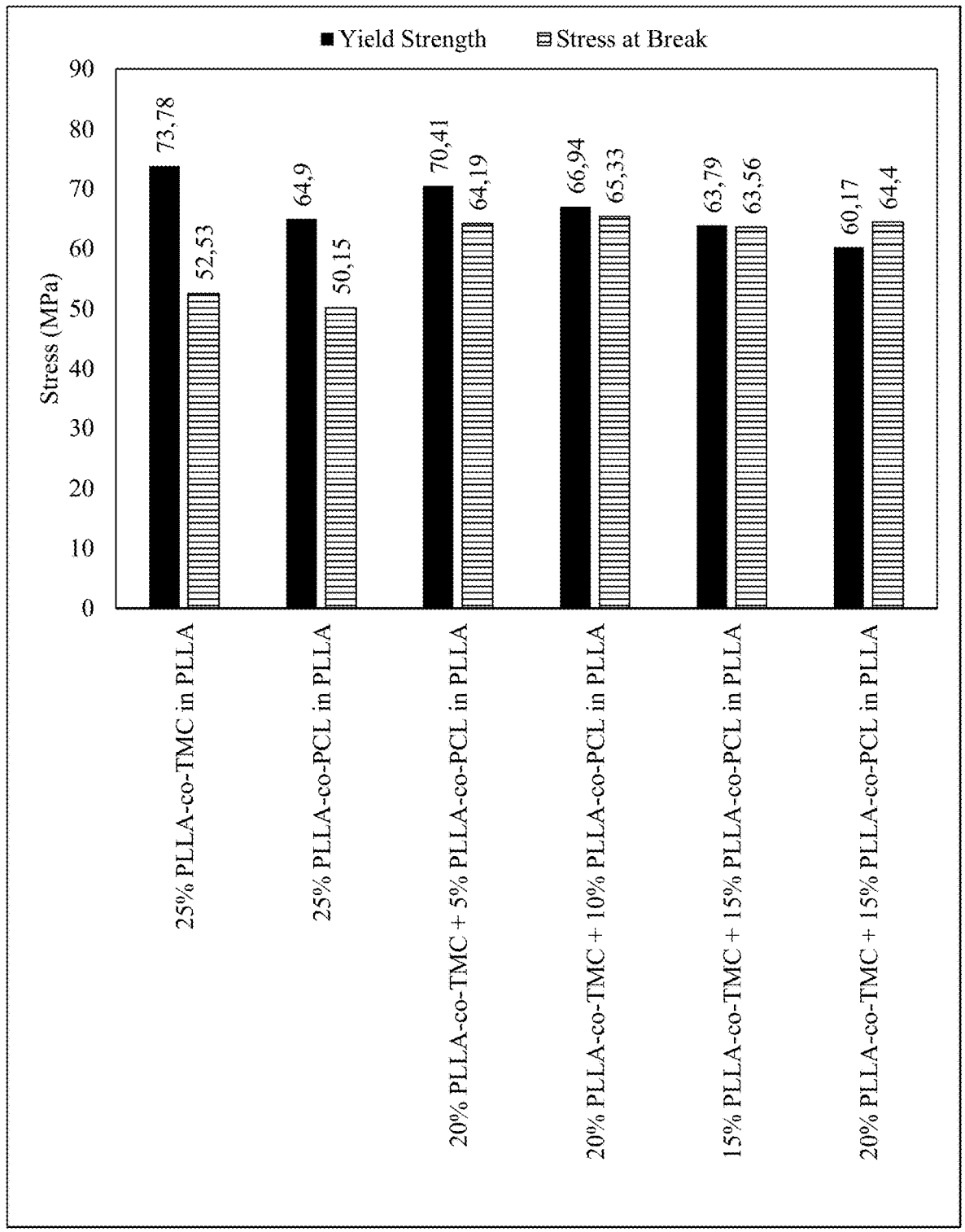
FIG. 7A depicts plastic stress behavior of PLLA binary blend with 25 wt % PLLA-co-TMC and PLLA binary blend with 25 wt % PLLA-co-PCL in comparison to PLLA ternary blends with varying levels of PLLA-co-TMC and PLLA-co-PCL from at 5 wt % to 20 wt % before and after annealing.
Figure 7B:
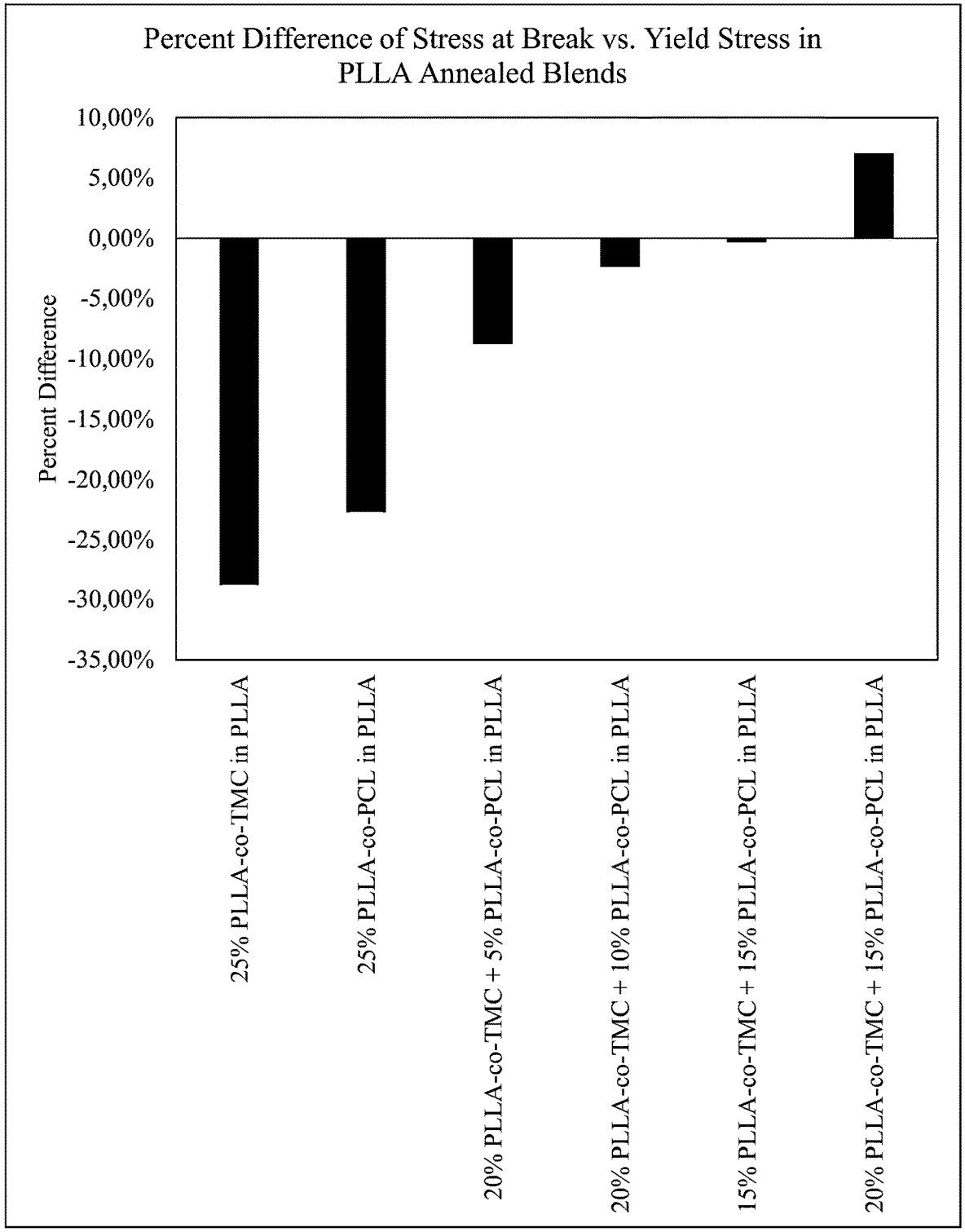
FIG. 7B depicts percent difference in stress at break vs yield stress for PLLA binary blends with 25 wt % PLLA-co-TMC additive polymer and PLLA binary blend with 25 wt % PLLA-co-PCL in comparison to PLLA ternary blends with varying levels of PLLA-co-TMC and PLLA-co-PCL from at 5 wt % to 20 wt % before and after annealing.

In one embodiment of this invention, mechanical properties of annealed specimens were compared with specimens before annealing. Binary blends of 75% PLLA with 25% PLLA-co-TMC as well as 75% PLLA with 25% PLLA-co-PCL exhibit significant strain softening with stress at break reduced from yield stress of 28% and 23% respectively. A ternary blend of 75% PLLA with 20% PLLA-co-TMC and 5% PLLA-co-PCL improved the strain softening behavior with reduction of stress at break from yield of 9%. Ternary blends of 70% PLLA with 20% PLLA-co-TMC and 10% PLLA-co-PCL and 70% PLLA with 15% PLLA-co-TMC and 15% PLLA-co-PCL exhibited elastoplastic behavior with percent difference of stress at break from yield stress of −2.41% and 0.36% respectively. A Ternary blend of 65% PLLA with 20% PLLA-co-TMC and 15% PLLA-co-PCL exhibited strain hardening behavior with stress at break higher than yield strength with an increase of 7.03% (FIG. 7).

Figure 8A:
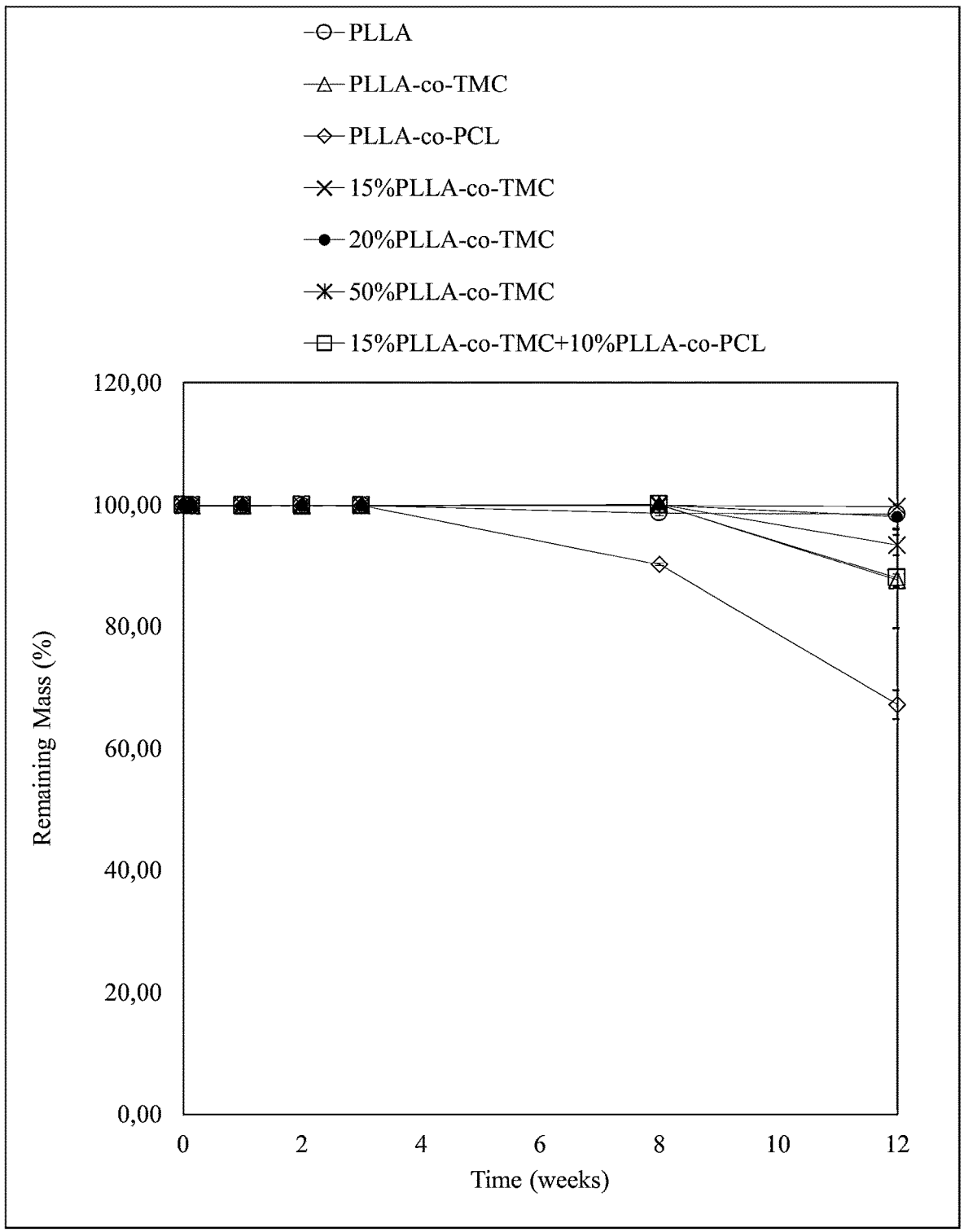
FIG. 8A depicts mass remaining of PLLA binary and ternary blends after accelerated degradation at 50° C. for 12 weeks.
Figure 8B:
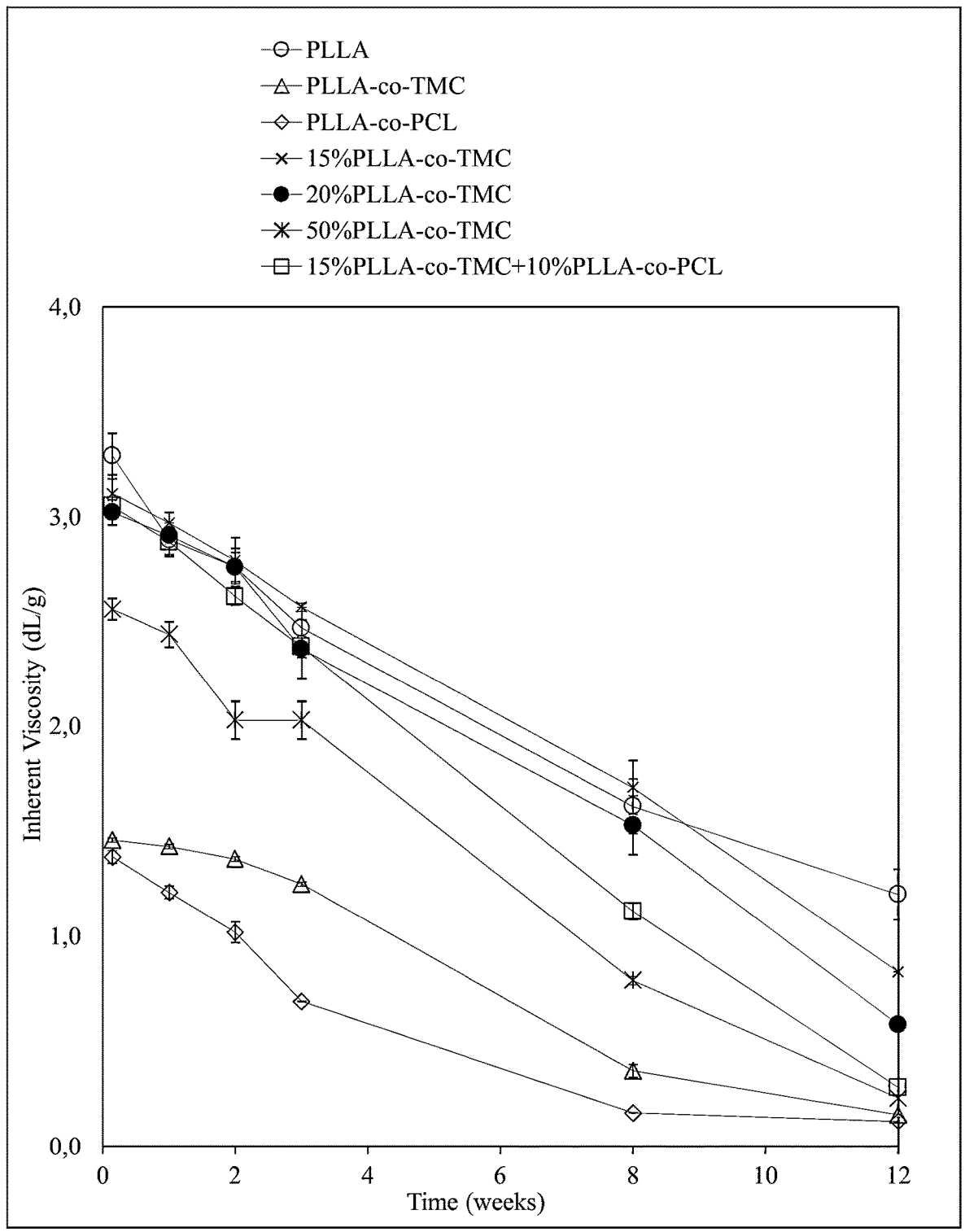
FIG. 8B depicts solution pH change of PLLA binary and ternary blends after accelerated degradation at 50° C. for 12 weeks.
Figure 8C:
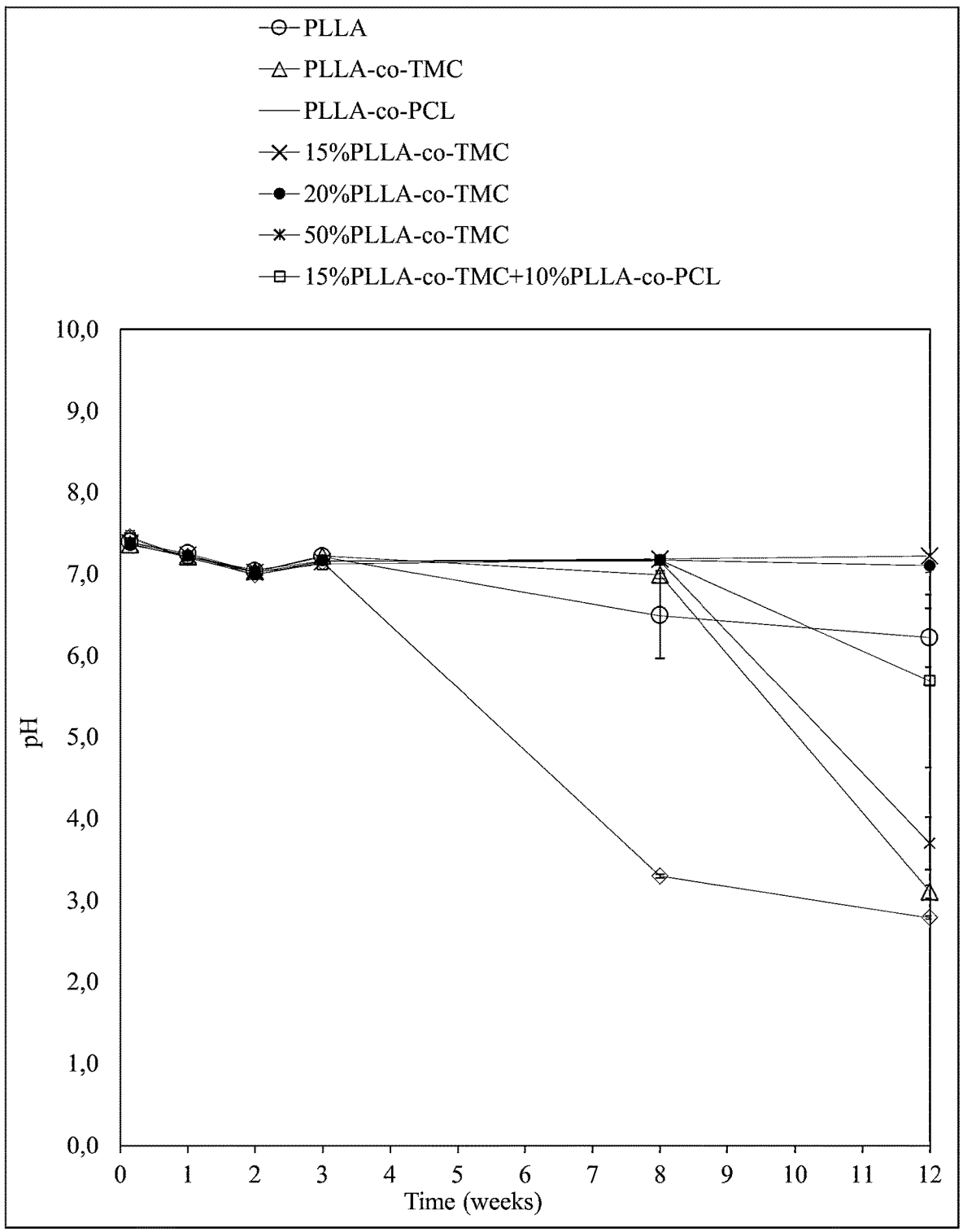
FIG. 8C depicts change in intrinsic viscosity (IV) of PLLA binary and ternary blends after accelerated degradation at 50° C. for 12 weeks.
Figure 8D:
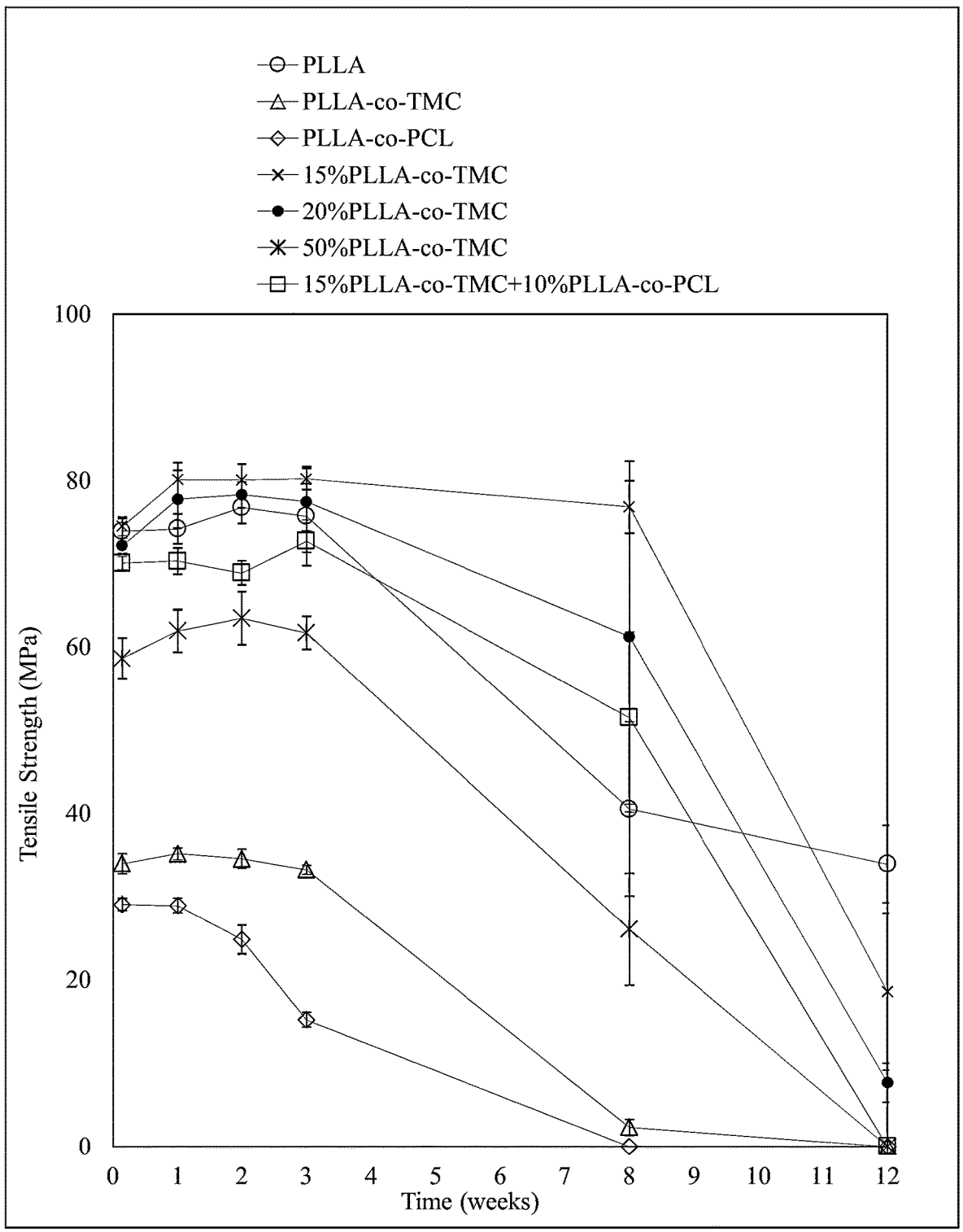
FIG. 8D depicts change in tensile strength of PLLA binary and ternary blends after accelerated degradation at 50° C. for 12 weeks.
Figure 8E:
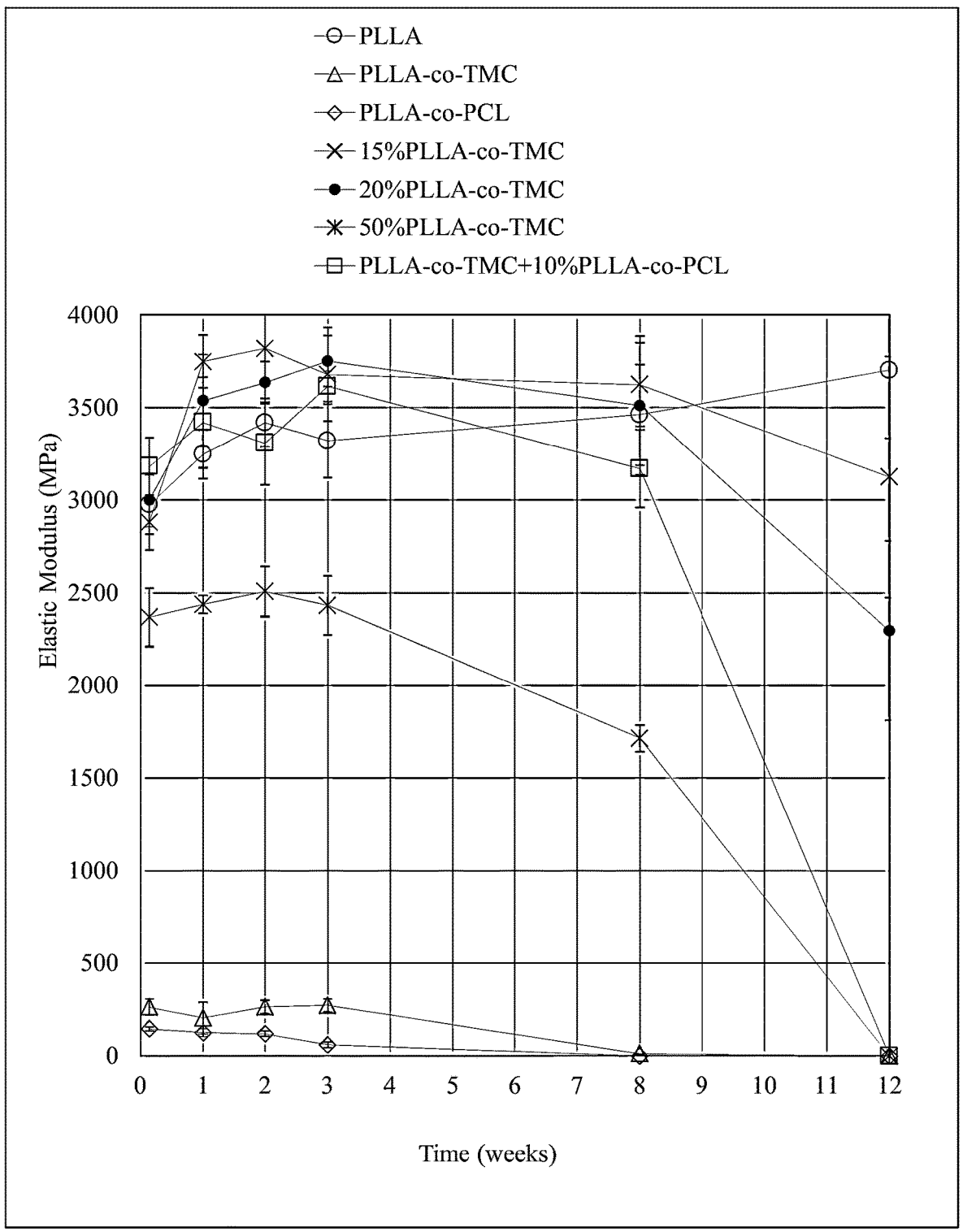
FIG. 8E depicts change in elastic modulus (stiffness) of PLLA binary and ternary blends after accelerated degradation at 50° C. for 12 weeks.

In another embodiment of this invention, accelerated degradation was conducted at 50° C. for 12 weeks. No changes in polymers mass were seen after 8 weeks in phosphate buffer saline (PBS) except for PLLA-co-PCL which seemed to have a slight mass loss (FIG. 8A). There was about 33% mass loss for PLLA-co-PCL and 1.5% degradation for PLLA base polymer after 12 weeks. The trend in Fig Xa exhibits increased mass loss with addition of polymer additives to the base polymer. Change in intrinsic viscosity (IV) shown in FIG. 8B confirmed a bulk degradation mechanism for all polymers in this invention. PLLA-co-PCL degraded faster than PLLA-co-TMC followed by polymer blend with 50% PLLA-co-TMC. Ternary polymer blend with 15% PLLA-co-TMC and 10% PLLA-co-TMC had similar degradation profile as binary blends with 20% and 15% PLLA-co-TMC up to 3 weeks and then degraded faster. These data indicate that base polymer degradation can increase with addition of polymer additives. Results in FIG. 8C also revealed a quick pH for PLLA-co-PCL from 7.4 to 3.3 after 8 weeks and to 2.79 after 12 weeks. There was a slower pH change for binary and ternary blends with additive polymers less than 50%. This could contribute to a higher biocompatibility. Mechanical test results revealed that all binary and ternary blends maintained a greater tensile strength as compared to PLLA base polymer with exception of binary blend with 50% PLLA-co-TMC up to 8 weeks (FIG. 8D). After 12 weeks, tensile strength of the above mentioned binary and ternary blends decreased to a greater extent. Elastic modulus in FIG. 8E showed a similar trend. The ternary blend with 15% PLLA-co-TMC and 10% PLLA-co-PCL had a sharp decrease in modulus after 8 weeks degradation.

Figure 9A:
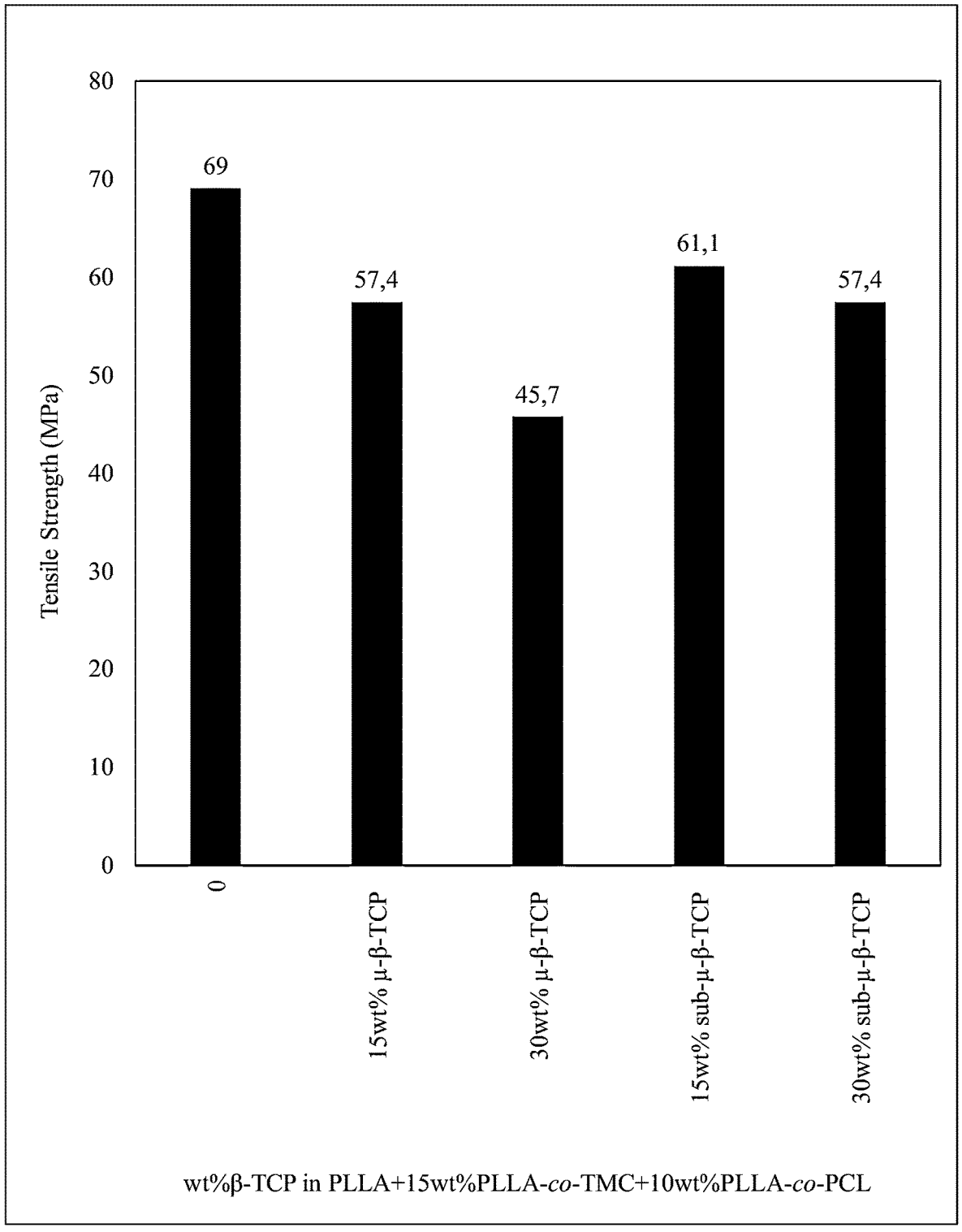
FIG. 9A depicts the effect on tensile strength after the addition of the inorganic additive β-tricalcium phosphate to the polymer weight-to-weight blends for orthopedic applications.
Figure 9B:
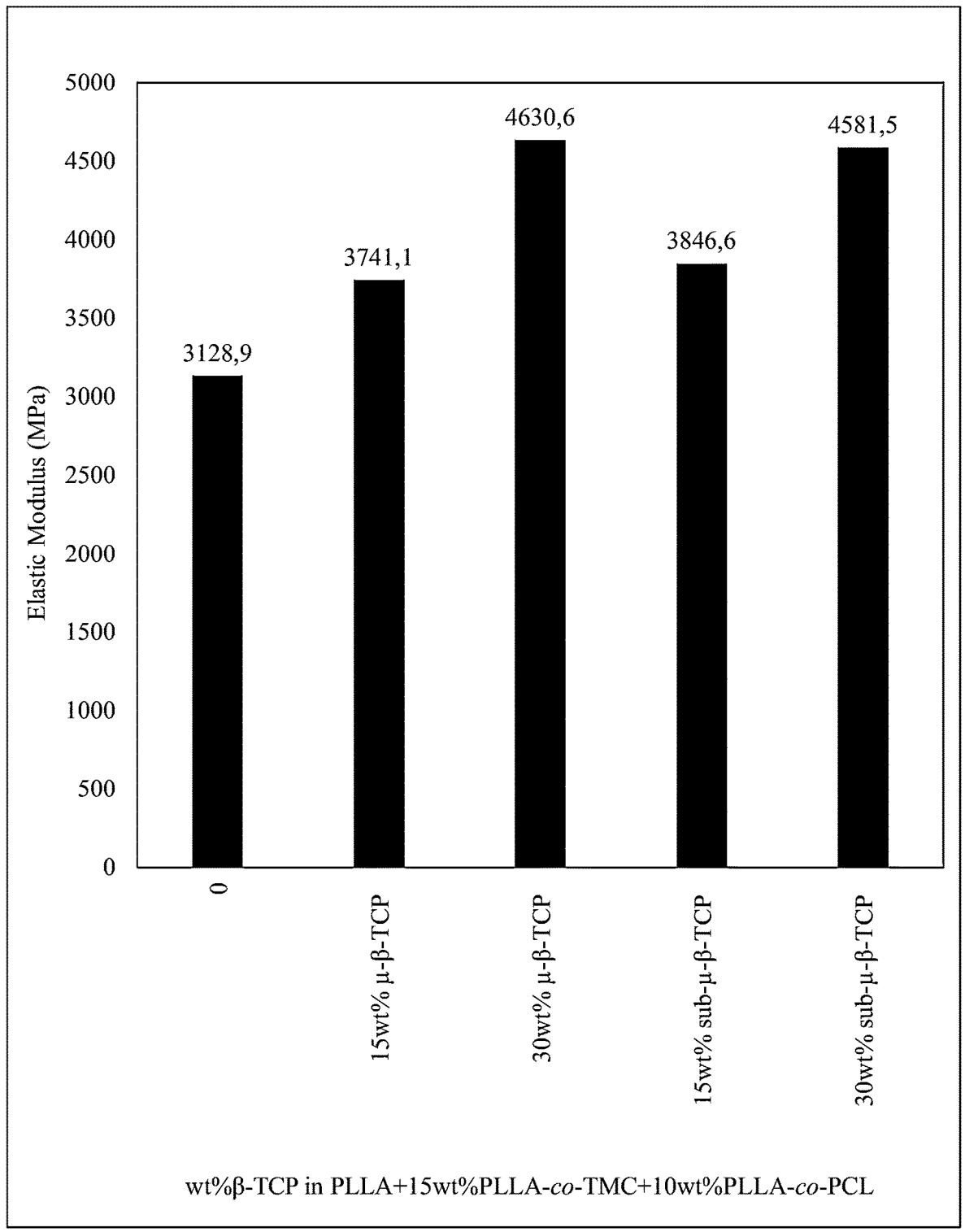
FIG. 9B depicts the effect on the elastic modulus after the addition of the inorganic additive β-tricalcium phosphate to polymer weight-to-weight blends for orthopedic applications.

In another embodiment of this invention, inorganic additives can be added to polymer blend using twin-screw extruder via melt blending. Similar to standard PLLA, there was change in mechanical properties when inorganic additives were added to the polymer blend PLLA+15 wt % PLLA-co-TMC+10 wt % PLLA-co-PCL. As shown in FIG. 9A, tensile strength of polymer blend decreased from 69 MPa with addition of 15% micro-β-TCP (D50 10 μm) and then changed to 45 MPa with increase in β-TCP concentration to 30%. Decrease in tensile strength was less when β-TCP with smaller particle size (500-700 nm) was added. As expected, modulus of polymer blends increased with addition of inorganic additives and this increase was a function of additive concentration as shown in FIG. 9B.

Figure 10A:
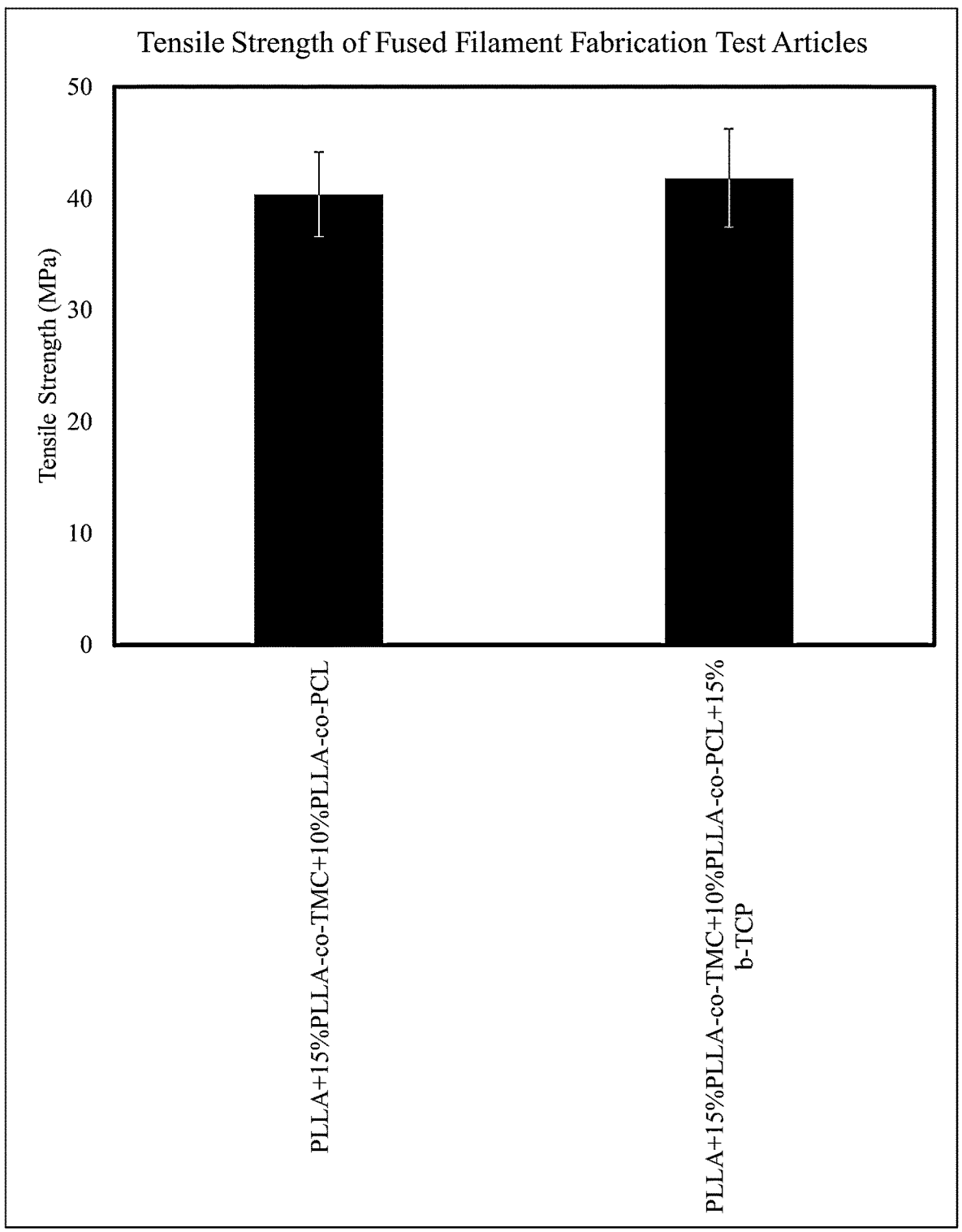
FIG. 10A depicts tensile strength of 3D printed PLLA ternary blend with 15 wt % PLLA-co-TMC and 10 wt % PLLA-co-PCL additive polymers in comparison to the same ternary blend incorporating 15% β-TCP
Figure 10B:
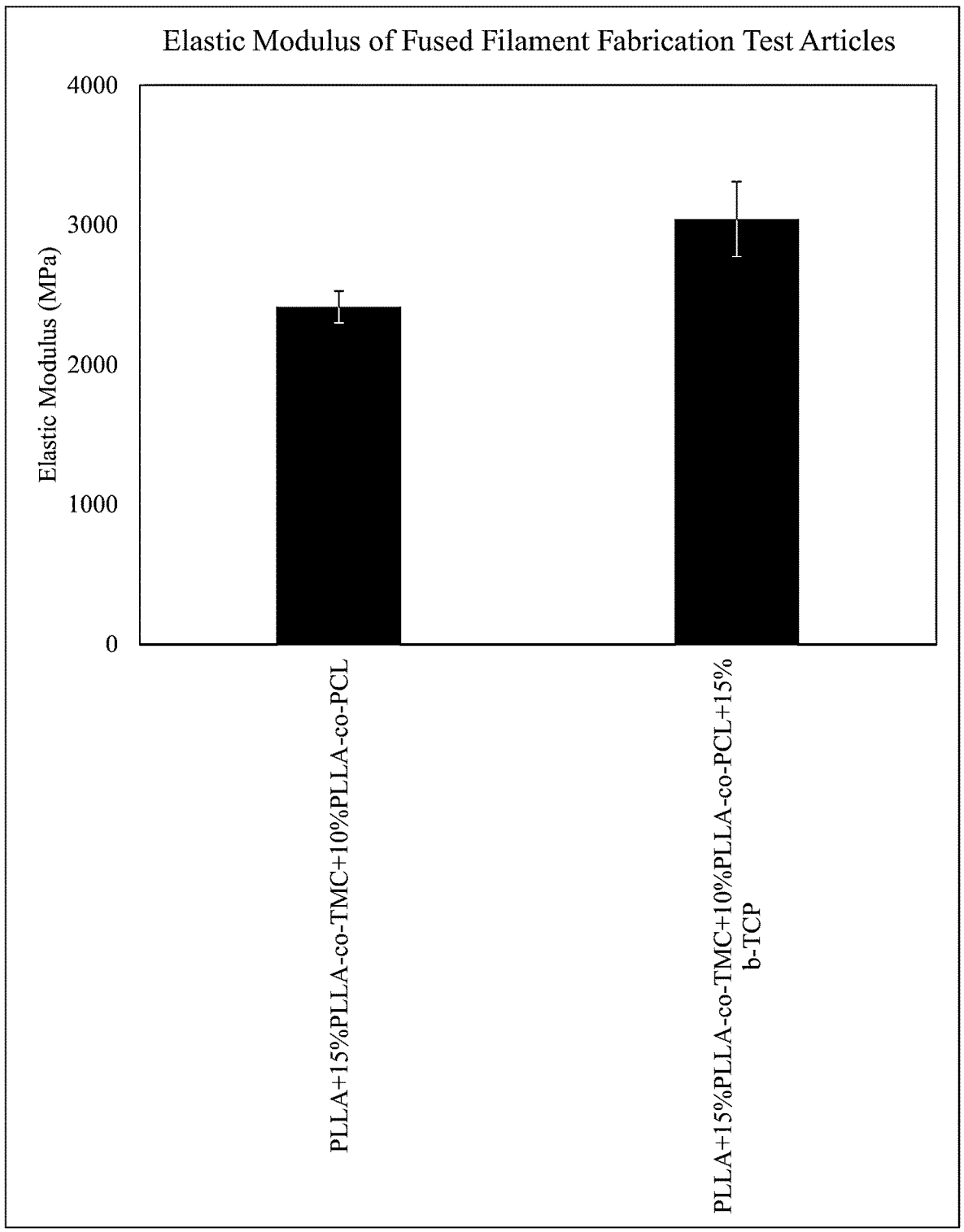
FIG. 10B depicts elastic modulus of 3D printed PLLA ternary blend with 15 wt % PLLA-co-TMC and 10 wt % PLLA-co-PCL additive polymers in comparison to the same ternary blend incorporating 15% β-TCP.

The ternary PLLA blend with 15 wt % PLLA-co-TMC and 10 wt % PLLA-co-PCL and their composite with 15% β-TCP were extruded into the filament with a diameter of 1.75 mm for FFF printing. The mechanical properties of 3D printed dog-bone specimens are shown in FIG. 10. A comparable tensile strength was observed for polymer blend with and without β-TCP (FIG. 10A). Elastic modulus of blend composite was greater than blend without β-TCP (FIG. 10B).

Figure 11A:
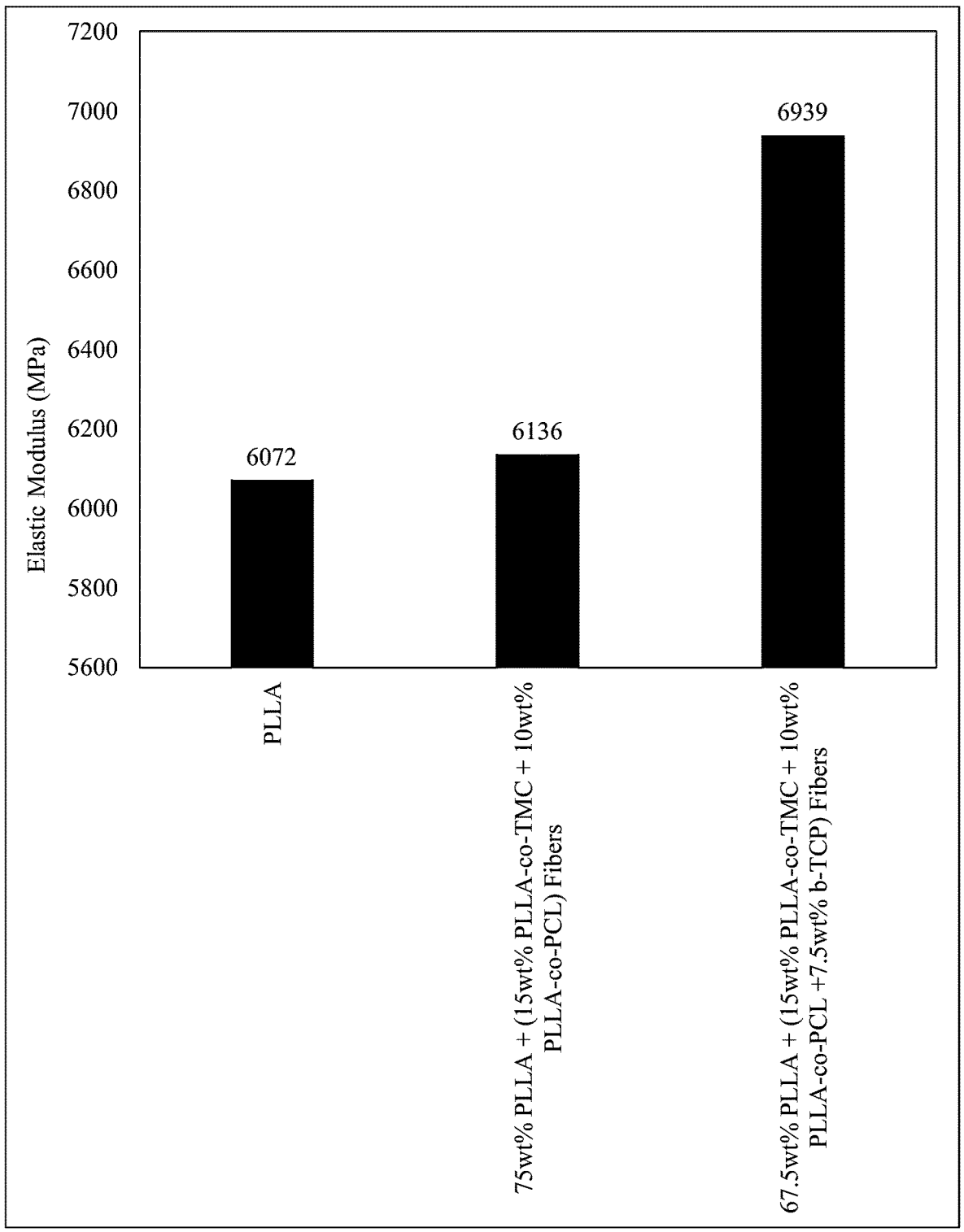
FIG. 11A depicts tensile elastic modulus of the extruded blend drawn fibers composed of 75 wt % PLLA+15 wt % PLLA-co-TMC+10 wt % PLLA-co-PCL compared to pure PLLA drawn fibers.
Figure 11B:
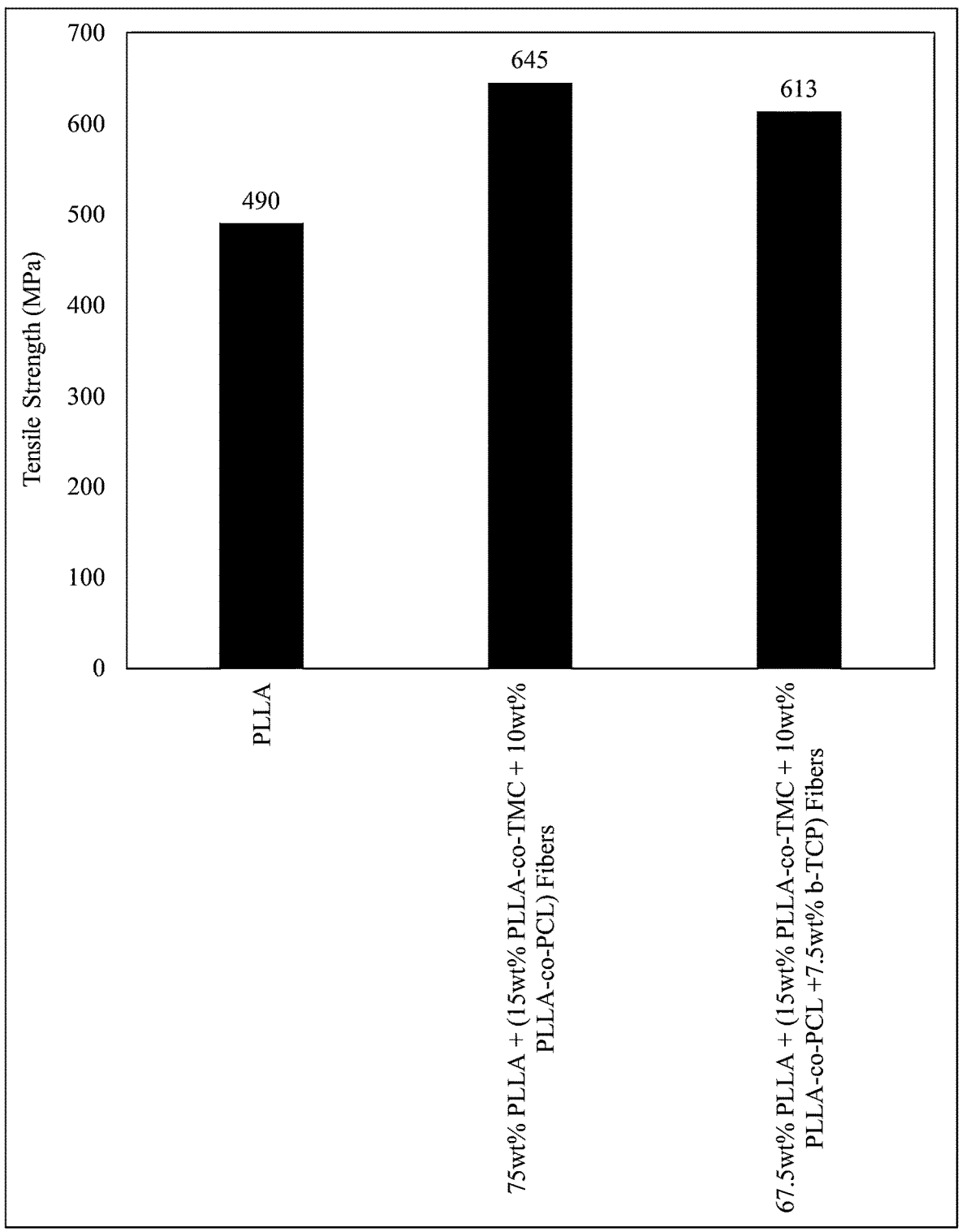
FIG. 11B depicts tensile strength of the extruded blend drawn fibers composed of 75 wt % PLLA+15 wt % PLLA-co-TMC+10 wt % PLLA-co-PCL compared to pure PLLA drawn fibers.
Figure 11C:
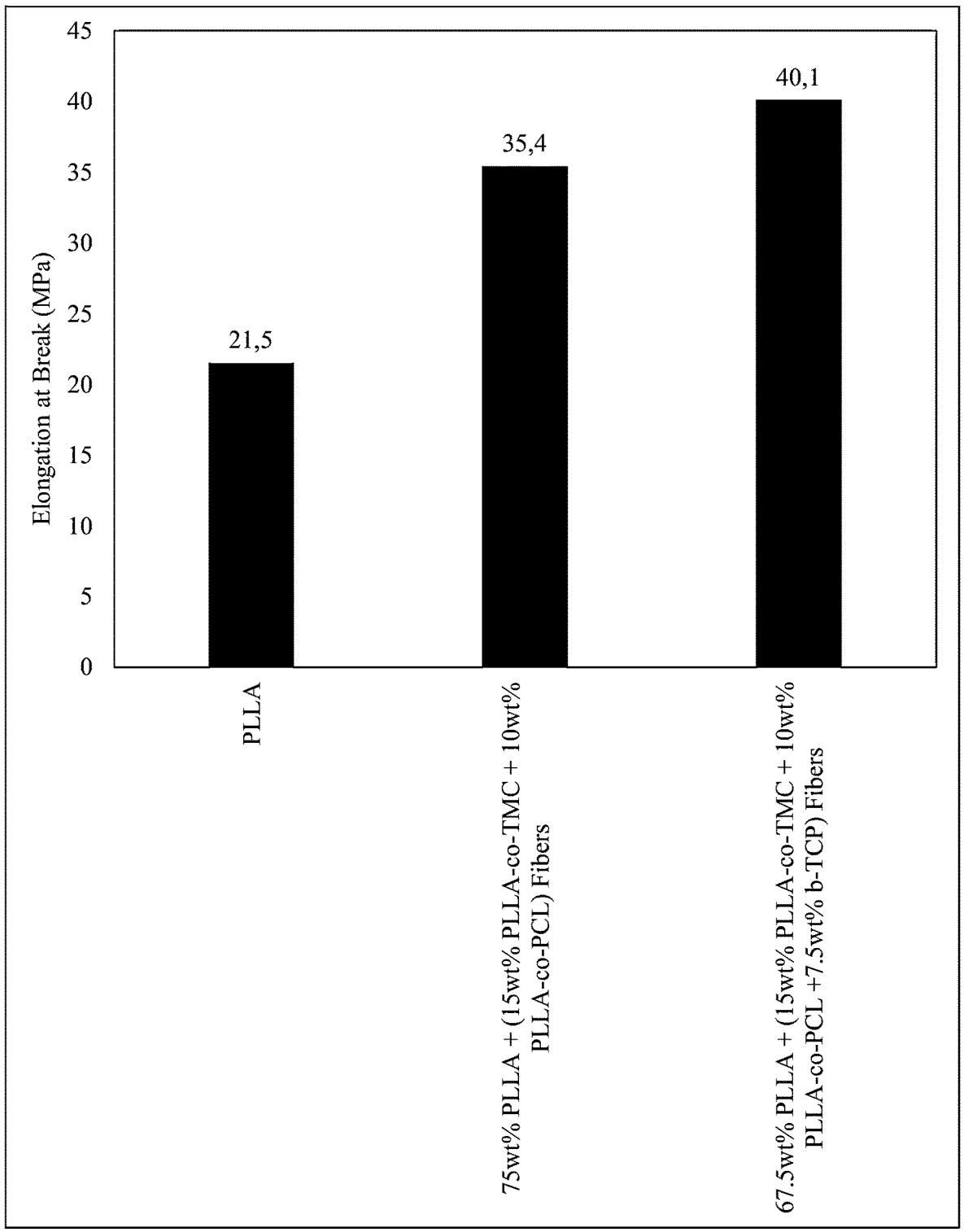
FIG. 11C depicts elongation at break of the extruded blend drawn fibers composed of 75 wt % PLLA+15 wt % PLLA-co-TMC+10 wt % PLLA-co-PCL compared to pure PLLA drawn fibers.

FIG. 11 reveals the mechanical properties of drawn fibers consisting of polymer blends and polymer blend composites containing 7.5% β-TCP. Mechanical testing indicated a tensile strength of 645 MPa for the drawn blend fibers and 613 MPa for the drawn blend composite fibers (FIG. 11A). Modulus of elasticity was 6136 for the drawn fiber blend and 6939 for the drawn blend composite fibers (FIG. 11B), with elongation at break of 35.4% for the drawn fiber blend and 40.1% for the drawn blend composite fibers (FIG. 11C).

In one aspects of this invention, fibers can be used for reinforcement of poly lactide polymer matrix and its blend with PLLA-co-TMC and PLLA-co-PCL. The degradable and non-degradable fibers include but not limited to PLLA, PGA, PLGA, PEEK, PVA, PET, PBT and PE. The fibers may be natural fibers including but not limited to silk, chitosan, chitin, keratin, and collagen. Processing includes compounding using twin-screw extruder and compression molding. In order to apply melt-processing technique such as extruder, compression molding and injection molding, fibers and polymer matrix should have completely distinct melting temperature ($T_m$). For example, PGA fibers with a $T_m$ of 230° C. can be processed with a polymer that has a temperature of melting that is at least 50° C. lower than fiber temperature of melting, but using a fiber with a $T_m$ of lower than 230° C. would be impossible. The polymer blends in this invention have lower temperature of melting as compare to their base suitable for fiber processing.

Figure 12A:
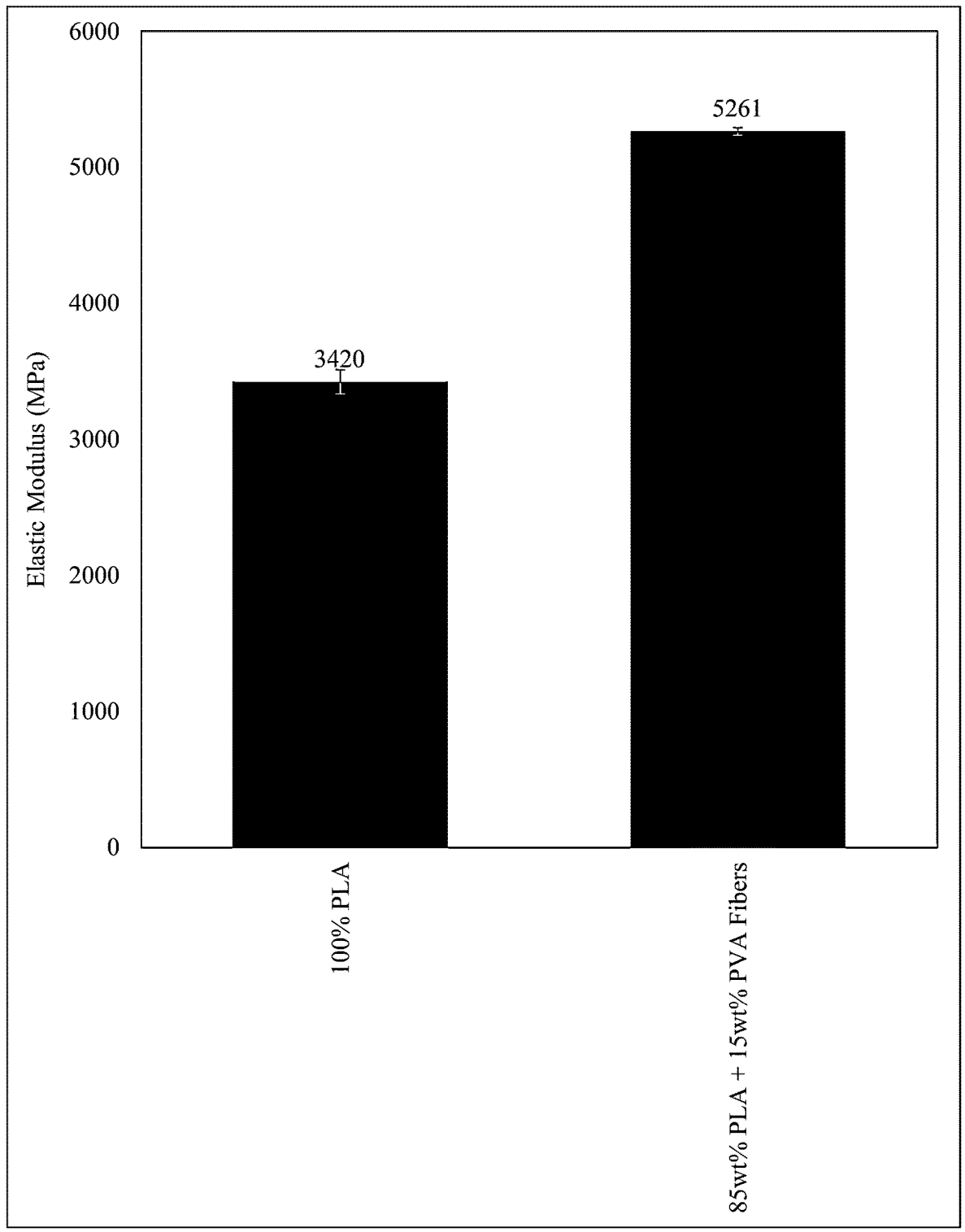
FIG. 12A depicts the effect of the effect of polyvinyl alcohol fiber concentration blended with PLLA matrix polymers on the elastic modulus of the polymer composites.
Figure 12B:
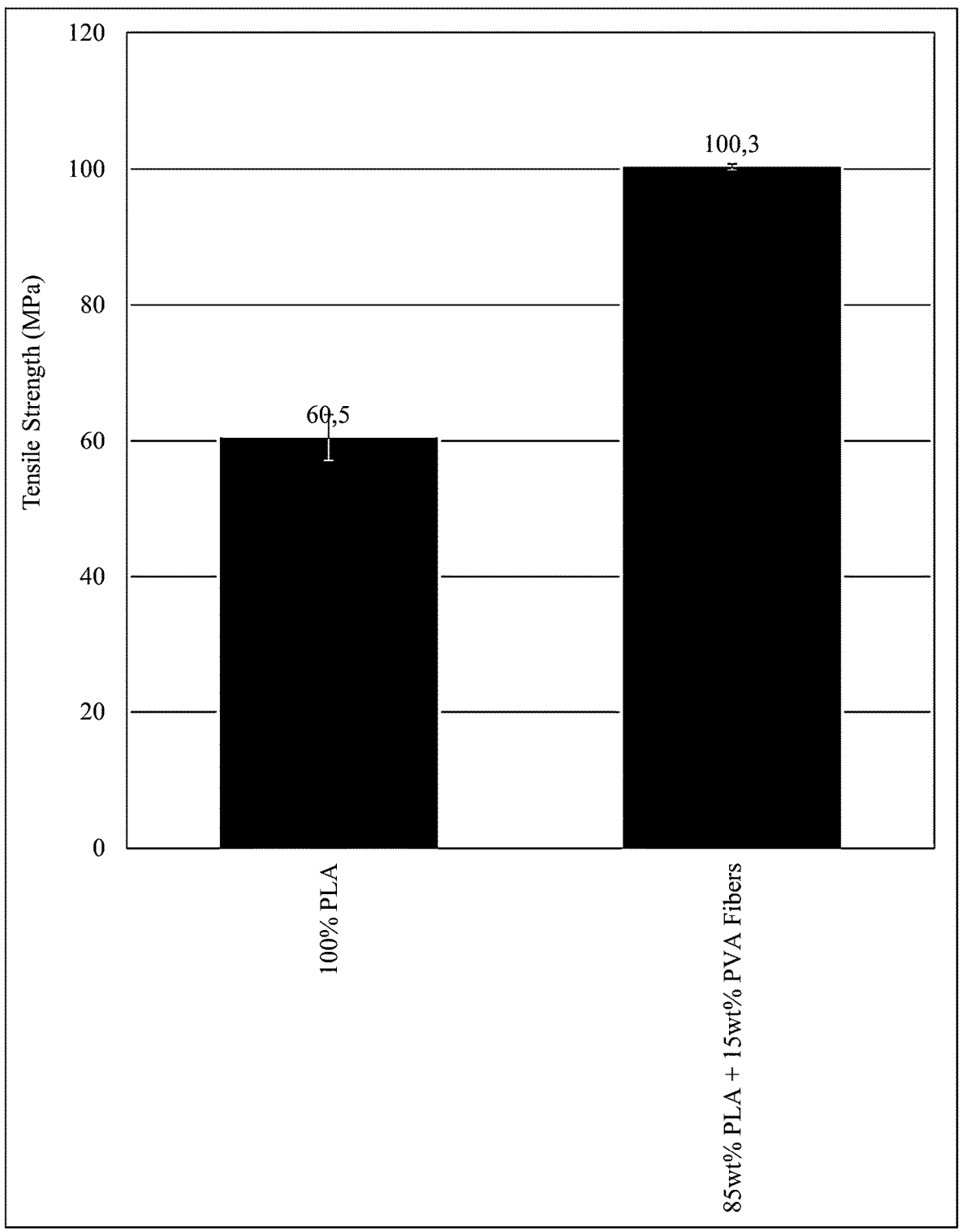
FIG. 12B depicts the effect of the effect of polyvinyl alcohol fiber concentration blended with PLLA matrix polymers on the tensile strength of the polymer composites.
Figure 12C:
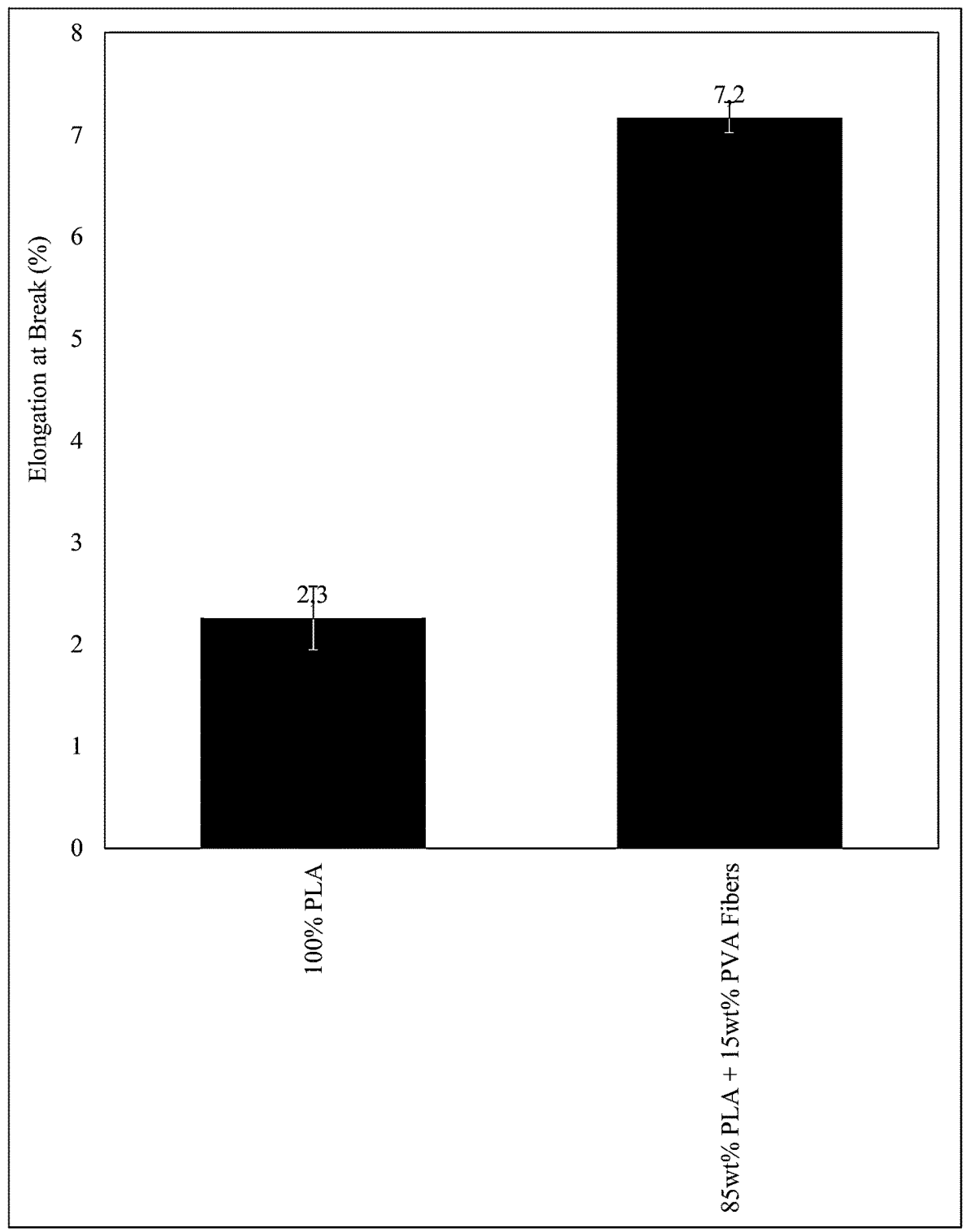
FIG. 12C depicts the effect of the effect of polyvinyl alcohol fiber concentration blended with PLLA matrix polymers on the tensile elongation at break of the polymer composites.

FIG. 12 reveals a composite of PVA fibers with PLA where the survival of fibers within the matrix after melt processing is confirmed. Mechanical testing indicates 59% increase in tensile strength of PLLA with addition of 15% PVA fibers (from 60 to 96 MPa) (FIG. 12A). Modulus of elasticity changed from 3.2 to 5.1 GPa (FIG. 12B), while elongation at break was also increased from 2% to 7% (FIG. 12C).

Figure 13A:
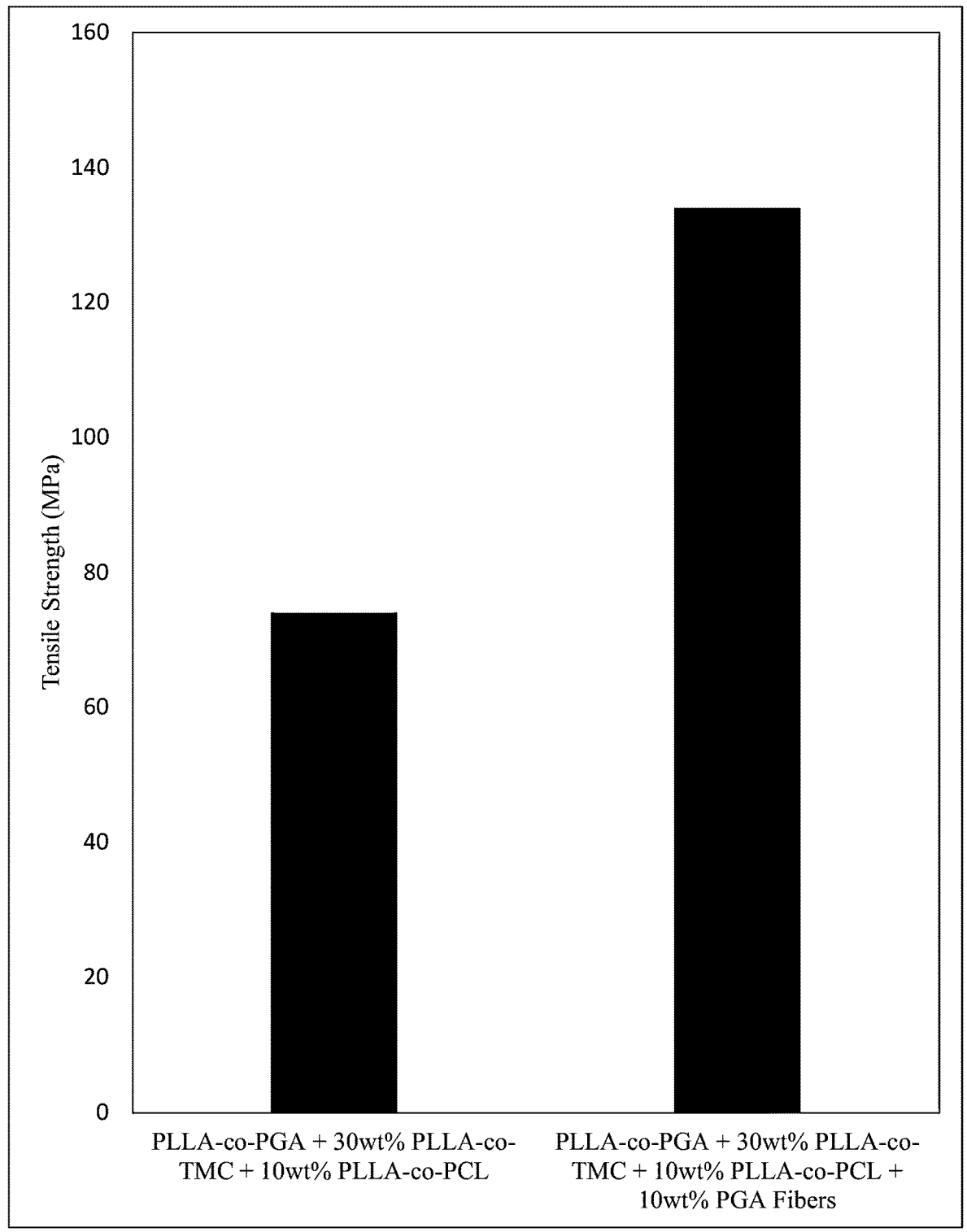
FIG. 13A depicts tensile strength of PLLA-co-PGA ternary blend with 30 wt % PLLA-co-TMC. and 10 wt % PLLA-co-PCL before and after combining with 10% PGA fibers
Figure 13B:
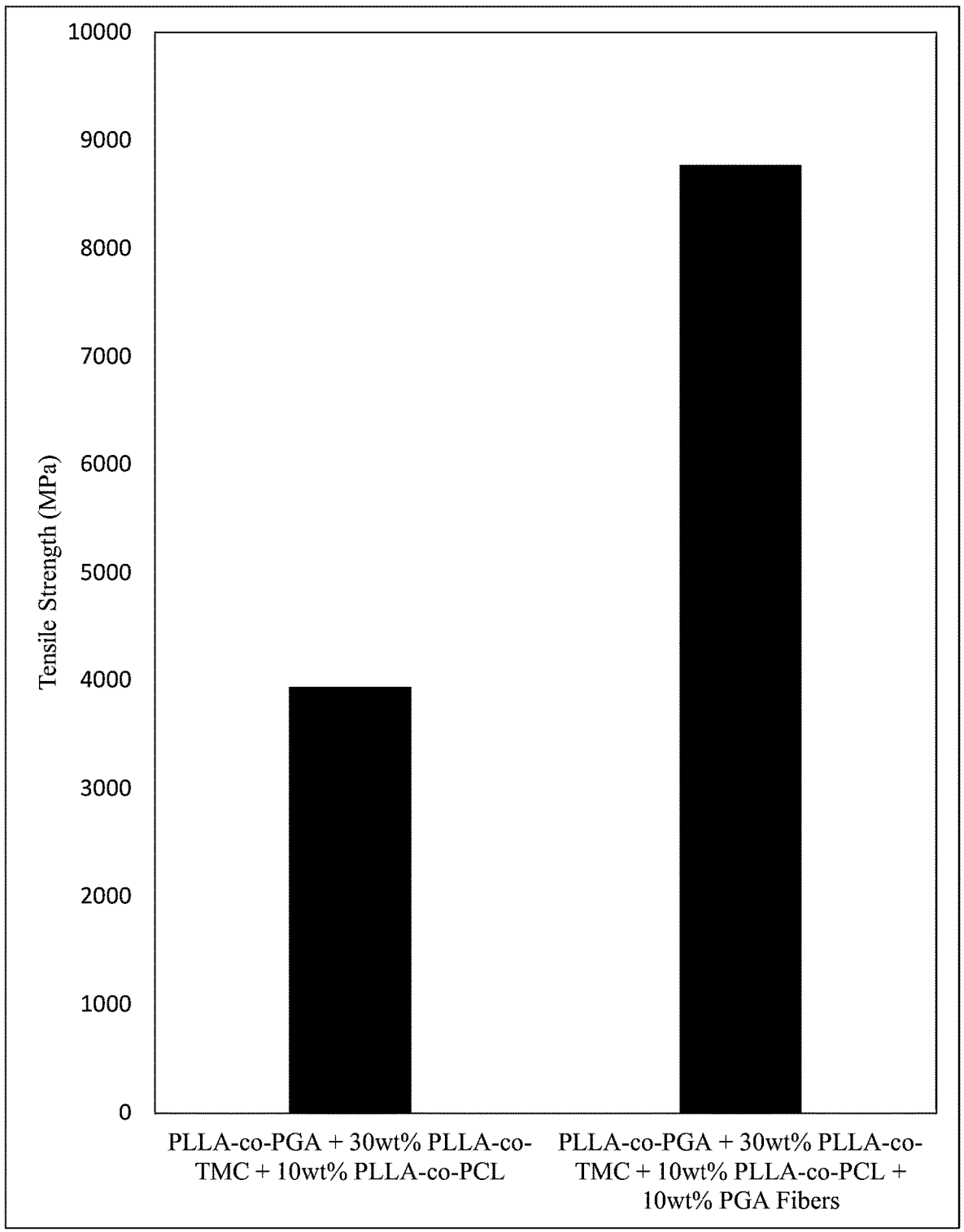
FIG. 13B depicts elastic modulus of PLLA-co-PGA ternary blend including 30 wt % PLLA-co-TMC and 10 wt % PLLA-co-PCL before and after combining with 10% PGA fibers.

A ternary polymer blend consisting PLLA-co-PGA as base polymer and a combination of additive polymers including 30 wt % PLLA-co-TMC and 15 wt % PLLA-co-PCL found to be suitable for PGA fiber processing at a temperature of 160° C. Mechanical properties of fiber reinforced composites are shown in FIG. 13. Tensile strength of unreinforced polymer blend was 74.06 MPa and it increased to 134.03 MPa with incorporation of 10% PGA fibers (FIG. 13A), and elastic modulus changed from 3942 MPa to 8778 MPa for PGA reinforced polymer blend (FIG. 13B). This example shows that using a blend with lower viscosity and melting point allows for incorporation of PGA fibers without melting the blended fiber.

EXAMPLES

The following examples are put forth so as to provide those of ordinary skill in the art with a complete disclosure and description of how the compositions, articles, and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

PLLA was blended with 15 wt % PLLA-co-TMC 70:30 and 10 wt % PLLA-co-PCL before being mechanically mixed through the use of a tumble mixer for 1 hour. The mixed material was then dried at a temperature of about 45° C. to reach of water moisture of between about 300 ppm as measured by an Arizona Computrac Vapor Pro moisture analyzer. The dried mixture was then extruded using hot-melt extrusion via a twin-screw compounder before being extruded and subsequently pelletized.

Example 2

The composition was made using thermal methods. Melt-processing through a Process 11 Thermo Scientific twin-screw compounding extruder was used to produce multi-component blends, and composites. The compositions were processed at a screw speed of 300 RPM, and heat zones and zone temperature in the range of 60° C. to 200° C. The subsequent extruded material was collected as a filament, and pelletized into 3 mm pellets for future processing through injection molding into test specimens.

The blended material pellets were then injection molded to a dog bone tensile specimen as described in ISO 527-2 1BA with a cross section of 5 mm×2 mm with and a test length of 58 mm. The prepared tensile samples were then aged in a desiccator at room temperature for 48 hours and tested according to the standard.

A differential scanning calorimetry (DSC-TA instrument Q2000) was used to test thermal behavior of polymer blend in endothermic and exothermic cycles. DSC was performed for three consecutive heat/cool/heat cycles. Each sample was preheated from room temperature to 200° C. at a heating rate of 10° C. $\min^{-1}$ and cooled to 25° C. at a cooling rate of 20° C. $\min^{-1}$. The last heating cycle was performed from 25 to 200° C. at a heating rate of 10° C. $\min^{-1}$. TA instrument Universal Analysis software was used to determine Tg, Tm and % crystallinity of polymer blend.

For NMR testing, samples were dissolved in $CDCl_3$ and a $^1H$ NMR spectrum was obtained from 400 MHz spectrometer.

Example 3

Everything remaining the same as in EXAMPLE 2, but additional post-processing steps were taken to further increase some of the mechanical properties of the blend. After aging at room temperature in a desiccator, the injection molded dog-bone samples of the blend composition were annealed at a temperature of 80° C. for 5 hours. At this time point, the samples were then cooled at a rate of 4° C./hr. The samples were mechanically tested as described below

Example 4

The data evaluation for the materials were prepared using similar methods as depicted in EXAMPLE 1 and EXAMPLE 2. Tensile testing on each of the materials were conducted. In accordance with ISO 527-1 Plastics-Determination of tensile properties, each sample being tested was loaded onto an Instron dual column universal testing machine Model 3366 fitted with a 10 kN load cell and pneumatic grips in order to determine the tensile strength, elongation, and modulus of the material. Per the standard the test speed for determination of modulus of elasticity was 0.2 mm/min and calculation of the elastic modulus was done over a strain range of 0.05% to 0.25%. Test speed for the remaining of the test was 5 mm/min until failure. Injection molded dog-bone samples were tested at a room temperature of 23° C.±2° C. The dog-bones were placed into clamps at a gauge length of 58 mm, and loaded with crosshead speed of 0.2 mm/min for the first 0.3% strain for modulus of elasticity calculation, and 5 mm/min afterwards for the rest of the tensile properties.

Example 5

Miscible blends of PLLA with varying concentrations of PLLA-co-TMC (15-20 wt %) and PLLA-co-PCL (5-15 wt %) were extruded via hot melt extrusion using methods outlined in previous examples. Tensile specimens were produced via injection molding the extruded material. For each blend half of the injection molded specimens were annealed at 80° C. for 5 hours. The specimens were aged for 2 days and tested in tension. Mechanical properties of annealed specimens were compared with specimens before annealing.

Example 6

For accelerated degradation, pure polymers including PLLA, PLLA-co-TMC, PLLA-co-PCL and polymer blends comprising PLLA and varying amounts of PLLA-co-TMC (15-50 wt %) and PLLA-co-PCL (10 wt %) were injection molded into tensile specimens (ISO 20753 A14) which have a cross sectional area of 2.5 mm×1 mm and a test length of 27.5 mm. The said tensile bars were placed in a 15 mL centrifuge tube containing 10 mL phosphate buffer saline (PBS), and incubated at 50° C. At each specific time point, specimens were taken out from PBS solution, and pH of solutions were measured. Mechanical testing was conducted on wet specimens, and tested specimens were placed in a vacuum oven overnight for mass loss and IV measurements.

Example 7

The polymer blend comprising 75% PLLA+15% PLLA-co-TMC+10 wt % PLLA-co-PCL was compounded with 30 wt % β-tricalcium phosphate. The resulting polymer blend composite was further processed through injection molding into articles for mechanical testing as well as medical device prototypes. This resulted in polymer blend containing inorganic additives for enhanced mechanical properties.

Example 8

Fabrication of monofilament fibers containing 75% PLLA, 15% PLLA-co-TMC, 10% PLLA-co-PCL blend, and the composite of same blend with 7.5% β-tricalcium phosphate (β-TCP) were processed using blend pellets described in EXAMPLE 1. In this process, the molten polymer strands are drawn via a winding mechanism under controlled temperature to produce drawn fibers. Mechanical properties of these fibers were further tested.

Example 9

A blend of 75% PLLA with 15% PLLA-co-TMC and 10% PLLA-co-PCL was extruded via hot melt extrusion using the methods outlined in previous examples. The extrudate was form into a 1.75 mm filament by adjusting a spooler rate of pull as the material came out of the extruder. The spooled filament was used in a fused filament fabrication (FFF) 3D printer to make feasibility samples. The samples were made using a nozzle temperature of 220° C. The bed of the printer was heated to 60° C. to improve first layer adhesion and the chamber was kept at 30° C.

Example 10

Fibers of PLLA (1.5 dpf×3.18 mm) and PVA (1.8 dpf× 6.35 mm) having similar bulk density where measured by weight to a ratio of 85:15% (PLLA:PVA). The fibers were then solid state blended using a high speed mixer. The fiber blend was then fed into an injection molding machine and injection molded into ISO 527-1 1BA specimens with a cross section of 5 mm×2 mm with and a test length of 58 mm. Injection molding was performed at a temperature below the melting point of the PVA fibers (237° C.) but above that of the PLLA fibers (180° C.). The resulting specimens were aged for two days at room temperature. Specimens were also manufactured this same way using only PLLA fibers with no reinforcing PVA. Modulus of elasticity for the unreinforced specimens was 3420 MPa compared to the PVA reinforced specimens value of 5128 MPa. Tensile Strength was 60.48 MPa for the PLLA specimens compared to the PVA reinforced PLLA with a value of 96.3 MPa. Finally the elongation at break was 2.265% and 6.88% for PLLA and PLLA-PVA reinforced respectively.

Example 11

A polymer mixture of 55% PLLA-co-PGA with 30% PLLA-co-TMC and 15% PLLA-co-PCL was blended via hot melt extrusion using a twin screw. The blend was re-extruded with PGA multifilament fibers incorporated into the compounding process at a temperature 160° C. which is 70° C. lower than the melting temperature of PGA fibers. The extruded material had a PGA concentration of 10%. Tensile bars were made out this material by injection molding the extrudate at 180° C. and subsequently tested following ISO 527 standards. Per the standard the test speed for determination of modulus of elasticity was 0.2 mm/min and calculation of the elastic modulus was done over a strain range of 0.05% to 0.25%. Test speed for the remaining of the test was 5 mm/min until failure.

Example 12

D&C #2 dye was added at a concentration of about 0.01 wt % to a polymer blend comprising 75 wt % PLGA, 15 wt % PLLA-co-TMC, and 10 wt % PLLA-co-PCL. The blending of the coloring agent was achieved through physical blending as powdered material of the coloring agent and subsequent mixing. The resulting colored polymer blend was melt processed using a twin screw extruder into 1.75 mm filaments suitable for free form fabrication 3D printing as well as pelletizing into 3 mm pellets for injection molding into medical device prototype.

Item 1 is a biodegradable polymer blend composition wherein the composition comprises:
at least one base polymer material; wherein the base polymer material is poly(lactic acid), poly(glycolic acid), isomers or copolymers thereof; and
at least one additive polymer material; wherein the additive polymer material is poly (lactide-co-caprolactone), poly (lactide-co-trimethylene carbonate), poly(lactide-co-dioxanone), poly (glycolide-co-caprolactone), poly(glycolide-co-trimethylene carbonate), poly(glycolide-co-dioxanone), isomers, or copolymers thereof.

Item 2 is the composition of claim 1, wherein the base polymer material is between 1 wt % and 50 wt %, and wherein the additive polymer material is between 50 wt % and 99 wt %.

Item 3 is the composition of claim 1 or 2, wherein the base polymer material, and additive polymer material are miscible.

Item 4 is the composition of claims 1 to 3, wherein the composition has a temperature of melting lower than the base polymer.

Item 5 is the composition of claims 1 to 4, wherein the composition has a melt temperature of about 150° C. to about 200° C.

Item 6 is the composition of claims 1 to 5, wherein the composition has an inherent viscosity of about 1.5 dL/g to about 4.5 dL/g.

Item 7 is the composition of claims 1 to 6, wherein the composition has an elongation at break ranging from 10% to 200%.

Item 8 is the composition of claims 1 to 7, wherein the base polymer material and the additive polymer material are blended together through melt processing into a multicomponent material.

Item 9 is the composition of claims 1 to 8, wherein the composition has cold-bendable properties at room temperature.

Item 10 is the composition of claims 1 to 9, wherein the composition retains at least 70% of its initial elongation at break properties after aging for 12 weeks.

Item 11 is the composition of claims 1 to 10, wherein the composition has a greater resistance to pH changes and loss of mechanical properties when compared to the base polymer throughout accelerated degradation.

Item 12 is the composition of claims 1 to 11, wherein the blended multicomponent material is homogenized via a compounding twin-screw extrusion process.

Item 13 is the composition of claims 1 to 12, can be processed into drawn monofilament and multifilament fibers.

Item 14 is the composition of claims 1 to 12, wherein the composition is formed into a semi-finished or finished medical device article.

Item 15 is the composition of claims 1 to 12, wherein the composition is processed into pellets, filaments, rods, or sheets.

Item 16 is the composition of claims 1 to 12, wherein the composition is processed by drawing into tubes or films.

Item 17 is the composition of claims 1 to 12, wherein the composition is used to form an article, and wherein the article is annealed.

Item 18 is the composition of claim 17, wherein the annealing increases the elastic modulus, tensile strength, and impact strength of the article as compared to the properties of an article consisting of base material.

Item 19 is the composition of claim 17, wherein the annealing changes the plastic deformation behavior of the material under loading from exhibiting strain softening behavior to strain hardening.

Item 20 is the composition of claim 17, wherein the annealing increases the stress at break by more than 40%.

Item 21 is the composition of claim 17, wherein the annealing increases the tensile strength above the yield strength of the base polymer.

Item 22 is the article of claim 17 is annealed at a temperature above the glass transition of the base polymer.

Item 23 is a biodegradable polymer blend composite composition for medical device applications wherein the polymer blend composite comprises:
  a. the composition of claim 1; and
  b. an additive material, wherein the additive material is particles, fibers, whiskers, inorganic additive, radiopaque materials, bioglass or combinations thereof.

Item 24 is the composition of claim 23, wherein the composition of claim 1 is between 50 wt % and 95 wt %, and wherein the additive material is between 5 wt % and 50 wt %

Item 25 is the composition of claim 23 or 24, wherein the additive material is inorganic additive; wherein the inorganic additive is apatites, calcium phosphates, calcium sulfates, inorganic salts, or any combination thereof.

Item 26 is the composition of claim 25, wherein the calcium phosphate salts contain a dopant; wherein the dopant is fluorine, strontium, magnesium, zinc, or a combination thereof.

Item 27 is the composition of claim 23 or 24, wherein the radiopaque materials is barium sulfate or tantalum.

Item 28 is the composition of claim 23 or 24, wherein the bioglass is Bioglass 45S.

Item 29 is the composition of claims 23 to 28, can be drawn into monofilament and multifilament fibers.

Item 30 is the composition of claim 29 wherein the said drawn fibers have a tensile strength of at least 1.5 times higher than fibers drawn out of the base polymer.

Item 31 is the composition of claim 23 to 28, wherein the composition increases the elastic modulus of the polymer blend composite as compared to the properties of the composition of claim 1.

Item 32 is the composition claim 23, 24, 25, or 28 wherein the inorganic additive material increases osteoconductivity of the composition.

Item 33 is the composition claim 23 or 24, wherein (a) and (b) are blended together through melt processing.

Item 34 is a fiber reinforced biodegradable polymer blend composite composition, wherein the fiber reinforced biodegradable polymer blend composite composition comprises:
  a. the composition of claim 1 or 23;
  b. fibers; and wherein the fibers is selected from the group consisting of poly(lactic acid), poly(glycolic acid), poly(lactide-co-glycolide), poly(caprolactone), poly(vinyl alcohol), polyether ether ketone (PEEK), polyethylene terephthalate (PET), polybutylene terephthalate (PBT), polyethylene (PE), silk, chitin, collagen, elastin, magnesium and magnesium alloys, or combinations thereof.

Item 35 is the composition of claim 34, wherein the composition of claim 1 is between 50 wt % and 99 wt %; and wherein the fibers is between 1 wt % and 50 wt %.

Item 36 is the composition of claim 34 or 35, wherein the fibers are continuous fibers, or chopped fibers.

Item 37 is the composition of claim 36, wherein the fibers have a diameter of less than 100 µm.

Item 38 is the composition of claim 36, wherein the chopped fibers have a length of about 1 mm to 30 mm.

Item 39 is the composition of claim 34 or 35, wherein the fibers are blended with the composition of claim 1 or 23 through melt processing.

Item 40 is the composition of claim 34 or 35, wherein the fibers increase the composite tensile strength and elastic modulus when compared to the composition of claim 1.

Item 41 is the composition of claim 34 or 35, wherein the composition is manufactured into a finished or semi-finished medical device article.

Item 42 is the composition of claim 34 or 35, wherein the composition is processed into pellets, filaments, rods, or sheets.

Item 43 is the composition of claim 34 or 35, wherein the composition is processed by drawing into tubes or films.

Item 44 is the composition of claim 34 or 35, wherein the composition is drawn into monofilament or multifilament fibers.

Item 45 is a biodegradable color polymer blend composition comprising:
  a. the composition of claim 1, 23 or 34; and
  b. a coloring agent.

Item 46 is the composition of claim 45, wherein the coloring agent is not less than 0.001 wt %.

Item 47 is the composition of claim 45 or 46, wherein the coloring agent is monosodium salt of 2-[(9,10-dihydro-4-hydroxy-9,10-dioxo-1-anthracenyl) amino]-5-methyl-benzenesulfonic acid (D&C Violet NO. 2), D&C Blue NO. 6, or D&C Green NO. 6.

Item 48 is the composition of claim 45 or 46 wherein (a) and (b) are blended together through melt processing into a multicomponent material.

Item 49 is the composition of claims 45 to 48, wherein the coloring agent is added for increased tracking during application.

Item 50 is the composition according to claims 1, 23, 34, and 45, wherein the composition is processed through additive manufacturing.

Item 51 is the composition of claim 50, wherein the additive manufacturing comprises bioplotter, fused filament fabrication (FFF), or selective laser sintering (SLS).

Item 52 is a process for making an article containing the composition of claims 1, 23, 34, or 45 comprising the steps of:
  a) mixing base polymer material and an additive polymer material to form a mixture;
  b) feeding the mixture into a twin-screw extruder;
  c) melting the mixture in the twin-screw extruder to form a extrudate;
  d) forming pellets from the extrudate; and
  e) injection molding of the extruded pellets into an article.

Item 53 is a process for making a filament containing the composition of any preceding claim, comprising the steps of:
  a) mixing of the individual components;
  b) feeding the mixture into a twin-screw extruder;
  c) melting the mixture in the twin-screw extruder to form an extrudate;
  d) pulling the extrudate to form a filament.

Item 54 is the composition of claim 53, wherein said filaments can be printed into articles using fused filament fabrication.

What is claimed is:

1. A biodegradable polymer blend composition wherein the composition comprises:
  one base polymer material; wherein the base polymer material is poly(lactic acid), poly(glycolic acid), isomers or copolymers thereof; and
  two additive polymer materials; wherein the additive polymer material is poly (lactide-co-caprolactone), poly(lactide-co-trimethylene carbonate), poly(lactide-co-dioxanone), poly(glycolide-co-caprolactone), poly(glycolide-co-trimethylene carbonate), poly(glycolide-co-dioxanone), isomers, or copolymers thereof, and wherein the base polymer material, and additive polymer materials
  i) are miscible; and/or
  ii) are blended together through melt processing into a multicomponent material.

2. The composition of claim 1, wherein the base polymer material is between 1 wt % and 50 wt %, and wherein the additive polymer material is between 50 wt % and 99 wt %.

3. A biodegradable polymer blend composition wherein the composition comprises:
  at least one base polymer material; wherein the base polymer material is poly(lactic acid), poly(glycolic acid), isomers or copolymers thereof; and
  at least one additive polymer material; wherein the additive polymer material is poly (lactide-co-caprolactone), poly(lactide-co-trimethylene carbonate), poly(lactide-co-dioxanone), poly (glycolide-co-caprolactone), poly (glycolide-co-trimethylene carbonate), poly(glycolide-co-dioxanone), isomers, or copolymers thereof, wherein the composition i) has a temperature of melting lower than the base polymer, and/or ii) has a melt temperature of about 150° C. to about 200° C.; and/or iii) has an inherent viscosity of about 1.5 dL/g to about 4.5 dL/g; and/or iv) has an elongation at break ranging from 10% to 200%; and/or v) has cold-bendable properties at room temperature; and/or vi) retains at least 70% of its initial elongation at break properties after aging for 12 weeks; and/or vii) has a greater resistance to pH changes and loss of mechanical properties when compared to the base polymer throughout accelerated degradation.

4. The composition of claim 1, wherein the composition i) can be processed into drawn monofilament and multifilament fibers; or ii) is formed into a semi-finished or finished medical device article; or iii) is processed into pellets, filaments, rods, or sheets; or iv) is processed by drawing into tubes or films; or v) is used to form an article, and wherein the article is annealed.

5. An article obtained by the composition of claim 1, wherein the article is annealed or wherein the article is annealed at a temperature above the glass transition of the base polymer.

6. A biodegradable polymer blend composite composition for medical device applications wherein the polymer blend composite comprises:
  a. the composition of claim 1; and
  b. an additive material, wherein the additive material is particles, fibers, whiskers, inorganic additive, radiopaque materials, bioglass or combinations thereof.

7. The composition of claim 6, wherein the composition of claim 1 is between 50 wt % and 95 wt %, and wherein the additive material is between 5 wt % and 50 wt %.

8. The composition of claim 6, wherein the additive material is inorganic additive; wherein the inorganic additive is apatites, calcium phosphates, calcium sulfates, inorganic salts, or any combination thereof.

9. A biodegradable polymer blend composition wherein the composition comprises:
  at least one base polymer material; wherein the base polymer material is poly(lactic acid), poly(glycolic acid), isomers or copolymers thereof; and
  at least one additive polymer material; wherein the additive polymer material is poly (lactide-co-caprolactone), poly(lactide-co-trimethylene carbonate), poly(lactide-co-dioxanone), poly (glycolide-co-caprolactone), poly (glycolide-co-trimethylene carbonate), poly(glycolide-co-dioxanone), isomers, or copolymers thereof, wherein the calcium phosphate salts contain a dopant; wherein the dopant is fluorine, strontium, magnesium, zinc, or a combination thereof.

10. The composition of claim 6, wherein the radiopaque materials is barium sulfate or tantalum.

11. A fiber reinforced biodegradable polymer blend composite composition, wherein the fiber reinforced biodegradable polymer blend composite composition comprises:
  a. the composition of claim 1;
  b. fibers; and wherein the fibers is selected from the group consisting of poly(lactic acid), poly(glycolic acid), poly (lactide-co-glycolide), poly(caprolactone), poly(vinyl alcohol), polyether ether ketone (PEEK), polyethylene terephthalate (PET), polybutylene terephthalate (PBT), polyethylene (PE), silk, chitin, collagen, elastin, magnesium and magnesium alloys, or combinations thereof.

12. The composition of claim 11, wherein the composition of claim 1 is between 50 wt % and 99 wt %; and wherein the fibers is between 1 wt % and 50 wt %.

13. The composition of claim 11, wherein the fibers i) are continuous fibers, or chopped fibers; or ii) the fibers have a diameter of less than 100 μm; or iii) are chopped fibers having a length of about 1 mm to 30 mm; or iv) are blended with the composition of claim 1 through melt processing; or v) increase the composite tensile strength and elastic modulus when compared to the composition of claim 1.

14. The composition of claim 11, wherein the composition i) is manufactured into a finished or semi-finished medical device article; or ii) is processed into pellets, filaments, rods, or sheets; or iii) is processed by drawing into tubes or films; or iv) is drawn into monofilament or multifilament fibers.

15. A biodegradable color polymer blend composition comprising:
  a. the composition of claim 1; and
  b. a coloring agent.

16. The composition of claim 15, wherein the coloring agent i) is not less than 0.001 wt %; and/or ii) is monosodium salt of 2-[(9,10-dihydro-4-hydroxy-9,10-dioxo-1-anthracenyl) amino]-5-methyl-benzenesulfonic acid (D&C Violet NO. 2), D&C Blue NO. 6, or D&C Green NO. 6.

17. A process for making an article containing the composition of claims 1 comprising the steps of:
  a) mixing base polymer material and an additive polymer material to form a mixture;
  b) feeding the mixture into a twin-screw extruder;
  c) melting the mixture in the twin-screw extruder to form a extrudate;
  d) forming pellets from the extrudate; and
  e) injection molding of the extruded pellets into an article.

18. A process for making a filament containing the composition of claim 1, comprising the steps of:
  a) mixing of the individual components;
  b) feeding the mixture into a twin-screw extruder;
  c) melting the mixture in the twin-screw extruder to form an extrudate;
  d) pulling the extrudate to form a filament.

* * * * *